United States Patent [19]

Tomita et al.

[11] 4,044,018

[45] Aug. 23, 1977

[54] ISOXAZOLONE DERIVATIVES, THEIR PREPARATION AND THEIR USE AS PLANT GROWTH REGULATORS

[75] Inventors: Kazuo Tomita, Yokosuka; Tadashi Murakami, Tokyo; Yoshio Yamazaki; Toyokuni Honma, both of Nozu, all of Japan

[73] Assignee: Sankyo Company Limited, Tokyo, Japan

[21] Appl. No.: 517,298

[22] Filed: Oct. 23, 1974

Related U.S. Application Data

[63] Continuation-in-part of Ser. No. 498,617, Aug. 19, 1974, abandoned, which is a continuation of Ser. No. 308,942, Nov. 24, 1972, abandoned.

[51] Int. Cl.$^2$ .......... C07D 261/12
[52] U.S. Cl. .......... 260/307 A; 71/88
[58] Field of Search .......... 260/307 A

[56] References Cited

U.S. PATENT DOCUMENTS 3,892,745 7/1975 Tomita et al. .......... 260/247.2 A

OTHER PUBLICATIONS

Mitsurube et al. - C. A. 73, 25440p (1970)–Abstract of Japanese Patent 10,144 of 4–11–70.

*Primary Examiner*—Raymond V. Rush
*Attorney, Agent, or Firm*—Toren, McGeady and Stanger

[57] ABSTRACT

Isoxazolone derivatives having the formula

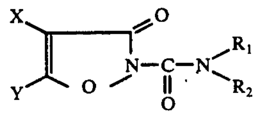

wherein X is hydrogen atom, a lower alkyl group or a halogen atom; Y is hydrogen atom, a lower alkyl group or phenyl group; and $R_1$ and $R_2$ may be the same or different and each represents a lower alkyl group, a cycloalkyl group, an alkeyl group, an alkoxycarbonylalkyl group, a cycloalkyl group, an alkenyl group, an alkynyl group, a lower alkoxy group, a phenyl group which may be substituted with one to three substituents or an aralkyl group which may be substituted with one to three substituents in the aryl moiety. They are useful as plant growth regulators, more specifically herbicides and plant growth retardants, and prepared by reacting the corresponding N-halogenocarbonylisoxazolone with an amine or by reacting the corresponding 3-hydroxyisoxazole with a carbamoyl halide.

14 Claims, No Drawings

ISOXAZOLONE DERIVATIVES, THEIR PREPARATION AND THEIR USE AS PLANT GROWTH REGULATORS

CROSS-REFERENCE TO PRIOR APPLICATIONS

This is a Continuation-in-Part of Ser. Number 498,617 filed Aug. 19, 1974, now abandoned, which in turn was a Continuation of Ser. No. 308,942 filed Nov. 24, 1972 and now abandoned.

SUMMARY OF THE INVENTION

This invention relates to a new group of isoxazolone derivatives, their preparation and their use as plant growth regulators.

More particularly, this invention is concerned with a new isoxazolone derivative having the formula (I)

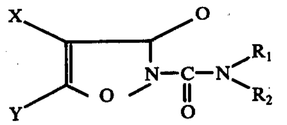

wherein X is hydrogen atom, a lower alkyl group or a halogen atom; Y is hydrogen atom, a lower alkyl group or phenyl group; and R1 and $R_2$ may be the same or different and each represents a lower alkyl group, a dialkoxyalkyl group, an alkoxycarbonyalkyl group, a cycloalkyl group, an alkenyl group, an alkynyl group, a lower alkoxy group, a phenyl group which may be substituted with one to three substituents or an aralkyl group which may be substituted with one to three substituents in the aryl moiety.

This invention is also concerned with a process for preparing the isoxazolone derivative having the above formula (I).

Further, this invention is concerned with a plant growth regulating composition which comprises as an active ingredient an effective amount, usually that of 0.1–99% by weight, based upon the composition, of the isoxazolone derivative having the above formula (I).

The term "plant growth regulating" as used herein means to include both "herbicidal" and "plant growth retarding" activities.

In the above formula (I), the lower alkyl group may be preferably of 1 to 6 carbon atoms and exemplified by methyl, ethyl, n-propyl, isopropyl, n-butyl, isobutyl, sec.-butyl, tert.-butyl, n-pentyl, isopentyl, or n-hexyl group; the halogen atom may be chlorine, bromine, fluorine or iodine atom; the dialkoxyalkyl group may be preferably of 1 to 3 carbon atoms in each alkoxy moiety and of 1 to 3 carbon atoms in the alkyl moiety and exemplified by dimethoxymethyl, diethoxymethyl, 2,2-dimethoxyethyl, 2,2-diethoxyethyl, di(n-propoxy) methyl or 3,3-dimethoxypropyl group; the alkoxycarbonylalkyl group may be preferably of 1 to 4 carbon atoms in the alkoxy moiety and of 1 to 2 carbon atoms in the alkyl moiety and exemplified by methoxycarbonylmethyl, ethoxycarbonylmethyl, n-propoxycarbonylmethyl, n-butoxycarbonylmethyl, 2-methoxycarbonylethyl, 2-ethoxycarbonylethyl, 2-n-propoxycarbonylethyl, 2-isobutoxycarbonylethyl, α-(methoxycarbonyl) ethyl, α-(ethoxycarbonyl)ethyl, α-(n-propoxycarbonyl)ethyl, α-(isopropoxycarbonyl)ethyl or α-(n-butoxycarbonyl)ethyl; the cycloalkyl group may be preferably of 5 to 7 carbon atoms and exemplified by cyclopentyl, cyclohexyl or cycloheptyl group; the alkenyl group may be preferably of 3 to 5 carbon atoms and exemplified by 2-propenyl, 1-methyl-2-propenyl, 2-methyl-2-propenyl, 2-butenyl, 1-methyl-2-butenyl, 2-methyl-2-butenyl, 3-butenyl, 1-methyl-3-butenyl or 2-methyl-3-butenyl group; the alkynyl group may be preferably of 3 or 4 carbon atoms and exemplified by 2-propynyl, 1-methyl-2-propynyl, 2-butynyl or 3-butynyl group; the lower alkoxy group may be preferably of 1 to 4 carbon atoms and exemplified by methoxy, ethoxy, n-propoxy, isopropoxy, n-butoxy, isobutoxy, sec.-butoxy or tert.-butoxy group; the substituted phenyl group may be illustrated by the formula

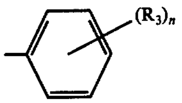

in which $R_3$ is a lower alkyl group, a halogen atom, a lower alkoxy group, an alkoxycarbonyl group, nitro group or trifluoromethyl group, *n* is an integer of 0 to 3 inclusive and R's may be the same or different; the substituted aralkyl group may be illustrated by the formula

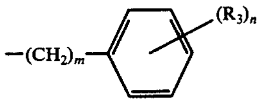

in which *n* and $R_3$ are as defined above and *m* is 1 or 2.

It has now been found that the isoxazoline derivatives of the formula (I) show potent herbicidal and plant growth retarding activities in pre- and post-emergence treatments. More specifically, they are highly effective against a wide variety of weeds belonging to, for instance, the families of Poaceae, Cyperaceae, Alismataceae, Scrophulariaceae, Brassicaceae, Lythraceae, Amaranthaceae, Portulacaceae, Chenopodiaceae, Commelinaceae, Lamiaceae, Oxalidaceae, Fabaceae, Euphorbiaceae and the like, especially those weeds belonging to the family Poaceae, e.g., manna-grass, cockspur-grass and the like, without any phytotoxicity against various beneficial plants. Also, they gave been found to have a good plant growth retarding activity on those plants, the unusual growth of which would not be desired, and thus they are effectively employed as growth retardants for turfs, for example, home-grown turfs, e.g., *Zoysia japonica* steudel, or *Zoysia tenuifolia* Willdenow and Western turfs, e.g., Bermuda grasses, bentgrasses, bluegrasses, fescues or ryegrasses. Further, they are highly effective against various weeds in an extremely small amount, which is unexpected to those skilled in the art.

It is, accordingly, an object of this invention to provide a new group of the isoxazolone derivatives of the above formula (I) which have a high plant growth regulating activity.

Another object of this invention is to provide a process for the preparation of the new and valuable isoxazolone derivatives (I).

Still another object of this invention is to provide herbicidal and plant growth retarding compositions which contain as an active ingredient an amount of 0.1 ~ 99% by weight, based upon the composition, of the isoxazolone derivative (I).

These and other objects and advantages of this invention will be apparent from the following description.

In one aspect of this invention, there is provided a group of the isoxazolone derivatives of the above formula (I) which are all new substances not disclosed in the prior art.

In view of herbicidal activity, for example, against cockspur-grass in a paddy field, preferable is the isoxazolone derivative having the formula

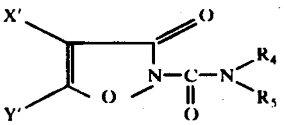

(II)

wherein X' is hydrogen atom, chlorine atom or bromine atom, Y' is hydrogen atom, methyl group or ethyl group, $R_4$ is allyl group or an alkyl group of 2 or 3 carbon atoms and $R_5$ is an alkyl group of 3 or 4 carbon atoms or a phenyl group which is substituted with one or two members selected from an alkyl group of 1 to 4 carbon atoms, a halogen atom, an alkoxy group of 1 to 4 carbon atoms, nitro group, an alkoxycarbonyl group of 1 to 4 carbon atoms in the alkoxy moiety and trifluoromethyl group.

Of the isoxazolone derivatives of the above formula (I), representative examples thereof are listed below, but they are not intended to be limiting the scope of this invention.

| Compound No. | Substituent X | Y | $R_1$ | $R_2$ | Physical Property |
|---|---|---|---|---|---|
| 1 | Cl | $CH_3$ | $CH_3$ | $CH_3$ | mp 133 ~ 134° C |
| 2 | Br | $CH_3$ | $CH_3$ | $CH_3$ | mp 94 ~ 95° C |
| 3 | Cl | $CH_3$ | $CH_3$ | $C_2H_5$ | $n_D^{22}$ 1.510 |
| 4 | Cl | $CH_3$ | $CH_3$ | n-$C_4H_9$ | $n_D^{21}$ 1.505 |
| 5 | Cl | $CH_3$ | $CH_3$ | 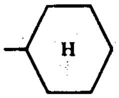 | mp 72.5 ~ 73.5° C |
| 6 | Cl | $CH_3$ | $CH_3$ | 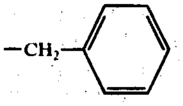 | mp 92.5 ~ 93.5° C |
| 7 | Cl | $CH_3$ | $CH_3$ | 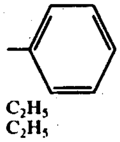 | mp 96 ~ 97° C |
| 8 | Cl | $CH_3$ | $C_2H_5$ | $C_2H_5$ | mp 88 ~ 90° C |
| 9 | Br | $CH_3$ | $C_2H_5$ | $C_2H_5$ | mp 58 ~ 60° C |
| 10 | Cl | $CH_3$ | $C_2H_5$ | 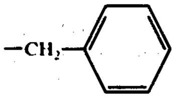 | $n_D^{24}$ 1.5435 |
| 11 | Cl | $CH_3$ | $C_2H_5$ | 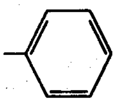 | mp 85 ~ 86.5° C |
| 12 | Cl | $CH_3$ | n-$C_3H_7$ | n-$C_3H_7$ | $n_D^{22}$ 1.4936 |
| 13 | H | H | n-$C_3H_7$ | n-$C_3H_7$ | mp 69° C |
| 14 | Cl | $CH_3$ | n-$C_3H_7$ | 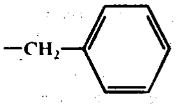 | mp 88.8 ~ 90.5° C |
| 15 | H | $CH_3$ | n-$C_3H_7$ | 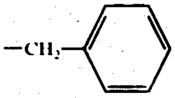 | mp 77.5 ~ 78.5° C |
| 16 | Cl | $CH_3$ | 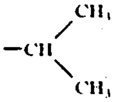 | 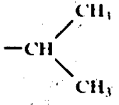 | mp 36.5 ~ 57.5° C |
| 17 | Cl | $CH_3$ | 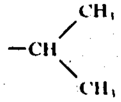 | 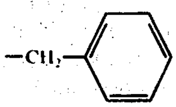 | mp 96.5 ~ 98.0° C |
| 18 | Cl | $CH_3$ | 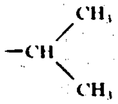 | 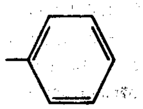 | mp 145° C |
| 19 | Cl | $CH_3$ | n-$C_4H_9$ | n-$C_4H_9$ | $n_D^{21}$ 1.493 |
| 20 | H | H | n-$C_4H_9$ | n-$C_4H_9$ | mp 37 ~ 37.5° C |

-continued
| Compound | Substituent | | | | Physical |
|---|---|---|---|---|---|
| No. | X | Y | $R_1$ | $R_2$ | Property |
| 21 | H | $CH_3$ | n-$C_4H_9$ | n-$C_4H_9$ | $n_D^{24}$ 1.4845 |
| 22 | Cl | $CH_3$ | n-$C_4H_9$ | 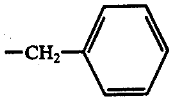 | mp 68~49° C |
| 23 | Cl | $CH_3$ | n-$C_4H_9$ | 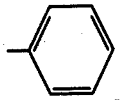 | mp 85.5~87.5° C |
| 24 | Cl | $CH_3$ | 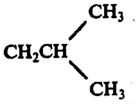 | 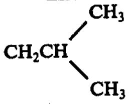 | $n_D^{24}$ 1.4889 |
| 25 | Cl | $CH_3$ | 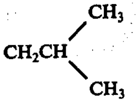 | 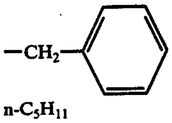 | mp 113.6~115.0° C |
| 26 | Cl | $CH_3$ | n-$C_5H_{11}$ | n-$C_5H_{11}$ | $n_D^{24}$ 1.4894 |
| 27 | Cl | $CH_3$ | 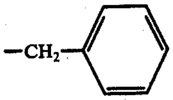 | 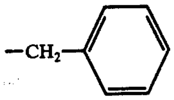 | mp 110~111.5° C |
| 28 | Cl | $CH_3$ | 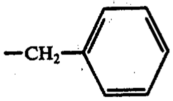 | 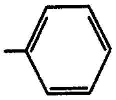 | mp 118~119° C |
| 29 | Cl | $CH_3$ | 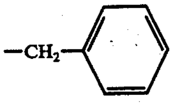 | 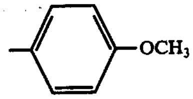 | mp 119~121° C |
| 30 | Cl | $CH_3$ | 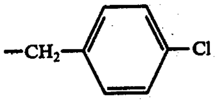 | 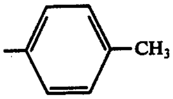 | mp 109~110° C |
| 31 | Cl | $CH_3$ | 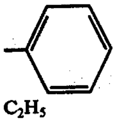 | 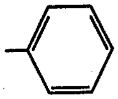 | mp 137~138.5° C |
| 32 | H | $CH_3$ | $C_2H_5$ | 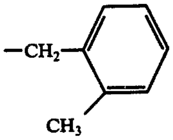 | mp 78~80° C |
| 33 | Cl | $CH_3$ | $C_2H_5$ | 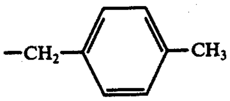 | $n_D^{20}$ 1.5475 |
| 34 | H | $CH_3$ | $C_2H_5$ | 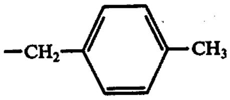 | mp 133~134° C |
| 35 | Cl | $CH_3$ | $C_2H_5$ | 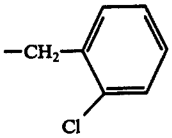 | mp 96.5~97.5° C |
| 36 | H | $CH_3$ | $C_2H_5$ | 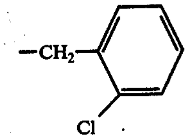 | mp 95.5~96° C |
| 37 | Cl | $CH_3$ | $C_2H_5$ | 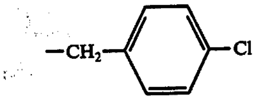 | mp 77~78° C |

-continued
| Compound No. | Substituent X | Y | $R_1$ | $R_2$ | Physical Property |
|---|---|---|---|---|---|
| 38 | H | $CH_3$ | $C_2H_5$ | 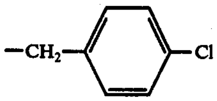 | mp 61 ~ 62° C |
| 39 | Cl | $CH_3$ | $C_2H_5$ | 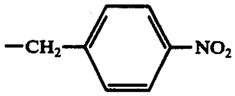 | mp 60 ~ 63.5° C |
| 40 | H | $CH_3$ | $C_2H_5$ | 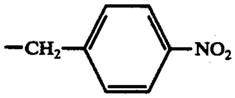 | mp 111 ~ 112° C |
| 41 | Cl | $CH_3$ | $C_2H_5$ | 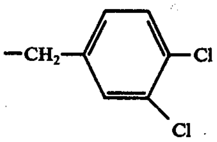 | mp 61.5 ~ 64° C |
| 42 | H | $CH_3$ | $C_2H_5$ | 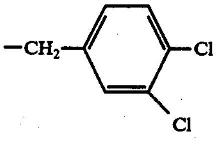 | mp 79 ~ 80° C |
| 43 | Cl | $CH_3$ | $C_2H_5$ | 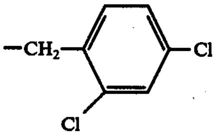 | mp 80.5 ~ 81.5° C |
| 44 | H | $CH_3$ | $C_2H_5$ | 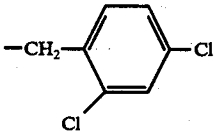 | mp 52 ~ 53° C |
| 45 | Cl | $CH_3$ | $(CH_2)_2CH_3$ | 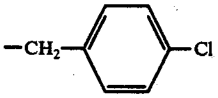 | $n_D^{21}$ 1.5566 |
| 46 | Cl | $CH_3$ | $CH(CH_3)_2$ | 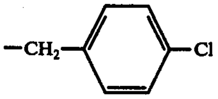 | $n_D^{21}$ 1.5637 |
| 47 | Cl | $CH_3$ | $(CH_2)_3CH_3$ | 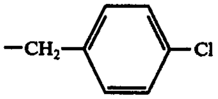 | $n_D^{21}$ 1.5460 |
| 48 | Cl | $CH_3$ | $CH_2CH(CH_3)_2$ | 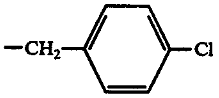 | mp 94 ~ 95° C |
| 49 | Cl | $CH_3$ | $CH(CH_3)CH_2CH_3$ | 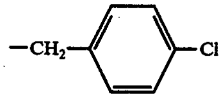 | mp 87 ~ 88° C |
| 50 | Cl | $CH_3$ | $CH_3$ | 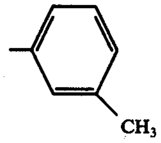 | mp 92.5 ~ 94.5° C |
| 51 | Cl | $CH_3$ | $CH_3$ | 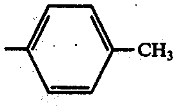 | mp 104.5 ~ 105.5° C |

-continued
| Compound | Substituent | | | | Physical |
|---|---|---|---|---|---|
| No. | X | Y | $R_1$ | $R_2$ | Property |
| 52 | Cl | $CH_3$ | $CH_3$ | 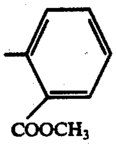 | mp 140~141.5° C |
| 53 | Cl | $CH_3$ | $CH_3$ | 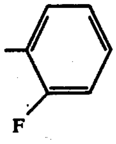 | mp 136~138° C |
| 54 | Cl | $CH_3$ | $C_2H_5$ | 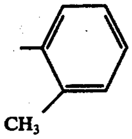 | mp 70~72° C |
| 55 | Cl | $CH_3$ | $C_2H_5$ | 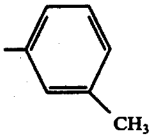 | mp 75~78° C |
| 56 | Cl | $CH_3$ | $C_2H_5$ | 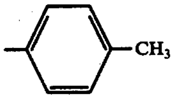 | mp 76.5~78° C |
| 57 | H | H | $C_2H_5$ | 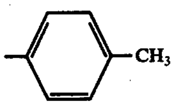 | mp 113~114° C |
| 58 | $CH_3$ | $CH_3$ | $C_2H_5$ | 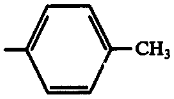 | mp 82~83° C |
| 59 | Cl | $CH_3$ | $C_2H_5$ | 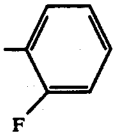 | mp 115.5~116.5° C |
| 60 | Cl | $CH_3$ | $C_2H_5$ | 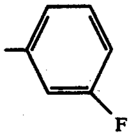 | mp 101° C |
| 61 | Cl | $CH_3$ | $C_2H_5$ | 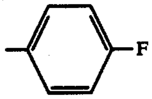 | mp 111..5~112° C |
| 62 | Cl | $CH_3$ | $C_2H_5$ | 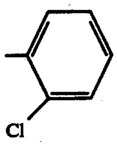 | mp 113~115° C |
| 63 | Cl | $CH_3$ | $C_2H_5$ | 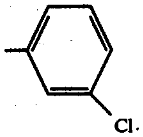 | mp 101~102° C |
| 64 | Cl | $CH_3$ | $C_2H_5$ | 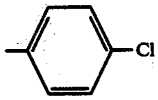 | mp 97~99° C |

-continued
| Compound No. | X | Y | $R_1$ | $R_2$ | Physical Property |
|---|---|---|---|---|---|
| | Substituent | | | | |
| 65 | Br | $CH_3$ | $C_2H_5$ | 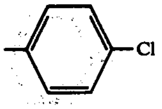 | mp 111~112° C |
| 66 | H | H | $C_2H_5$ | 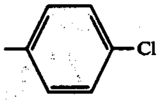 | mp 149° C |
| 67 | $CH_3$ | $CH_3$ | $C_2H_5$ | 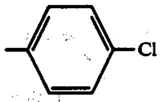 | mp 117~118° C |
| 68 | $CH_3$ | $CH_3$ | $C_2H_5$ | 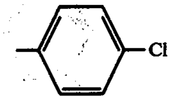 | mp 90~91° C |
| 69 | Cl | $C_2H_5$ | $C_2H_5$ | 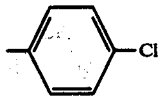 | mp 90~92° C |
| 70 | Cl | $CH_3$ | $C_2H_5$ | 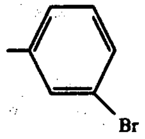 | mp 97.5~99° C |
| 71 | Cl | $CH_3$ | $C_2H_5$ | 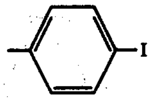 | mp 125~128° C |
| 72 | Cl | $CH_3$ | $C_2H_5$ | 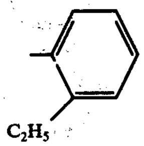 | $n_D^{20}$ 1.5518 |
| 73 | Cl | $CH_3$ | $C_2H_5$ | 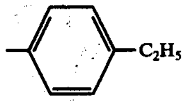 | $n_D^{20}$ 1.5529 |
| 74 | Cl | $CH_3$ | $C_2H_5$ | 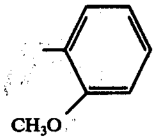 | mp 95~96° C |
| 75 | Cl | $CH_3$ | $C_2H_5$ | 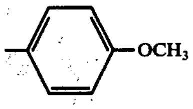 | mp 102.5~103.5° C |
| 76 | H | H | $C_2H_5$ | 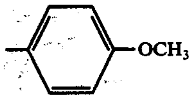 | mp 101~102° C |
| 77 | Cl | $CH_3$ | $C_2H_5$ | 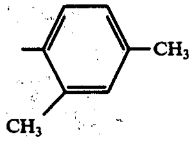 | mp 71~74.5° C |
| 78 | Cl | $CH_3$ | $C_2H_5$ | 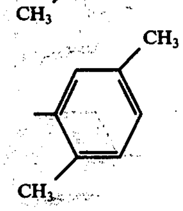 | mp 96~99° C |

-continued
| Compound No. | Substituent X | Y | $R_1$ | $R_2$ | Physical Property |
|---|---|---|---|---|---|
| 79 | Cl | $CH_3$ | $C_2H_5$ | 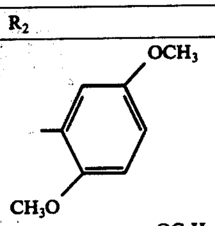 | mp 117.5~119.5° C |
| 80 | Cl | $CH_3$ | $C_2H_5$ | 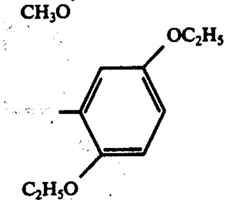 | mp 94~95° C |
| 81 | Cl | $CH_3$ | $C_2H_5$ | 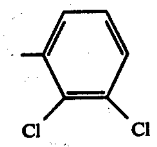 | mp 105~106° C |
| 82 | Cl | $CH_3$ | $C_2H_5$ | 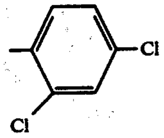 | mp 101~102° C |
| 83 | H | H | $C_2H_5$ | 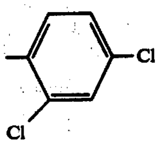 | mp 145° C |
| 84 | Cl | $CH_3(CH_2)_2$ | $C_2H_5$ | 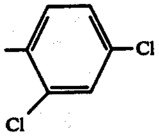 | mp 102~102.5° C |
| 85 | Cl | $CH_3$ | $C_2H_5$ | 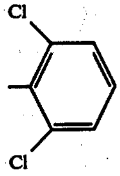 | mp 139~142° C |
| 86 | Cl | $CH_3$ | $C_2H_5$ | 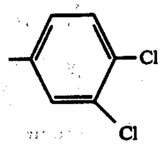 | mp 129.5~132.5° C |
| 87 | Cl | $CH_3$ | $C_2H_5$ | 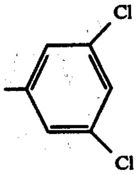 | mp 118~121° C |
| 88 | Cl | $CH_3$ | $C_2H_5$ | 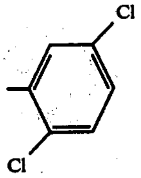 | mp 112.5~113.5° C |
| 89 | Cl | $CH_3$ | $C_2H_5$ | 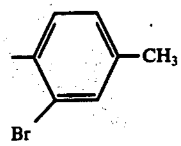 | mp 78.5~80° C |

-continued
| Compound | Substituent | | | | Physical |
|---|---|---|---|---|---|
| No. | X | Y | $R_1$ | $R_2$ | Property |
| 90 | Cl | $CH_3$ | $C_2H_5$ | 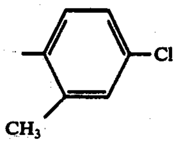 | mp 83.5~85.5° C |
| 91 | Cl | $CH_3$ | $C_2H_5$ | 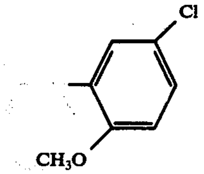 | mp 128~129.5° C |
| 92 | Cl | $CH_3$ | $C_2H_5$ | 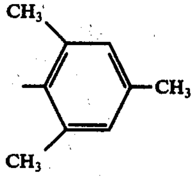 | mp 77.5~78.5° C |
| 93 | Cl | $CH_3$ | $(CH_2)_2CH_3$ | 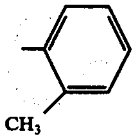 | mp 67~68° C |
| 94 | Cl | $CH_3$ | $(CH_2)_2CH_3$ | 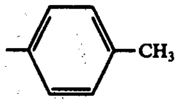 | mp 75~76° C |
| 95 | Cl | $CH_3$ | $(CH_2)_2CH_3$ | 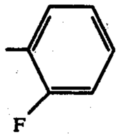 | mp 113~113.5° C |
| 96 | Cl | $CH_3$ | $(CH_2)_2CH_3$ | 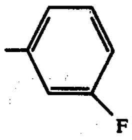 | mp 121° C |
| 97 | Cl | $CH_3$ | $(CH_2)_2CH_3$ | 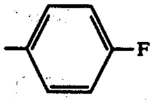 | mp 80~80.5° C |
| 98 | Cl | $CH_3$ | $(CH_2)_2CH_3$ | 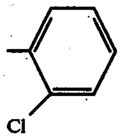 | mp 100~102° C |
| 99 | H | H | $(CH_2)_2CH_3$ | 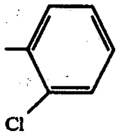 | mp 121.5~122° C |
| 100 | H | $CH_3$ | $(CH_2)_2CH_3$ | 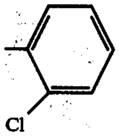 | mp 73.8~74.4° C |
| 101 | Cl | $C_2H_5$ | $(CH_2)_2CH_3$ | 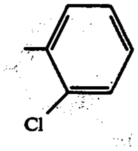 | mp 92~93° C |

-continued
| Compound | Substituent | | | | Physical |
| --- | --- | --- | --- | --- | --- |
| No. | X | Y | $R_1$ | $R_2$ | Property |
| 102 | Cl | $CH_3(CH_2)_2$ | $(CH_2)_2CH_3$ | 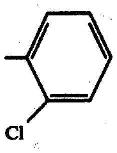 | $n_D^{26}$ 1.5402 |
| 103 | Cl | $CH_3$ | $(CH_2)_2CH_3$ | 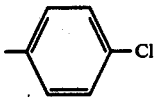 | mp 98~99° C |
| 104 | Cl | $CH_3$ | $(CH_2)_2CH_3$ | 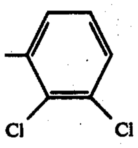 | mp 101.2~102.1° C |
| 105 | Cl | $CH_3$ | $(CH_2)_2CH_3$ | 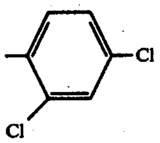 | mp 85.6~86.8° C |
| 106 | Cl | $CH_3$ | $CH(CH_3)_2$ | 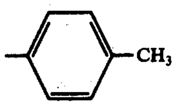 | mp 114.5~115.5° C |
| 107 | Cl | $CH_3$ | $CH(CH_3)_2$ | 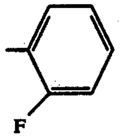 | mp 149~150° C |
| 108 | Cl | $CH_3$ | $CH(CH_3)_2$ | 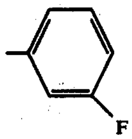 | mp 119~120° C |
| 109 | Cl | $CH_3$ | $CH(CH_3)_2$ | 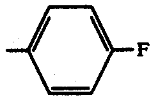 | mp 141.5° C |
| 110 | Cl | $CH_3$ | $CH(CH_3)_2$ | 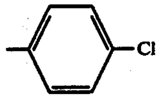 | mp 136~137° C |
| 111 | Cl | $C_2H_5$ | $CH(CH_3)_2$ | 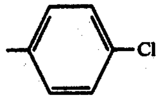 | mp 120~121° C |
| 112 | Cl | $CH_3(CH_2)_2$ | $CH(CH_3)_2$ | 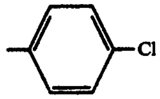 | mp 93~94° C |
| 113 | Cl | $CH_3$ | $CH(CH_3)_2$ | 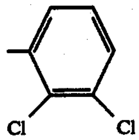 | mp 185~187° C |
| 114 | Cl | $CH_3$ | $CH(CH_3)_2$ | 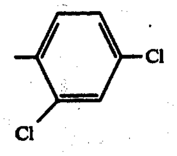 | mp 144~144.5° C |

-continued

| Compound No. | Substituent X | Y | $R_1$ | $R_2$ | Physical Property |
|---|---|---|---|---|---|
| 115 | Cl | $CH_3$ | $(CH_2)_3CH_3$ | 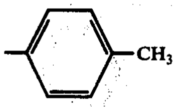 | mp 57~58° C |
| 116 | Cl | $CH_3$ | $(CH_2)_3CH_3$ | 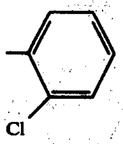 | mp 91~91.5° C |
| 117 | Cl | $CH_3$ | $(CH_2)_3CH_3$ | 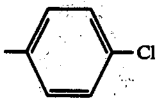 | mp 69~71° C |
| 118 | Cl | $CH_3$ | $(CH_2)_3CH_3$ | 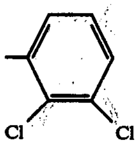 | mp 81.5~82.3° C |
| 119 | Cl | $CH_3$ | $(CH_2)_3CH_3$ | 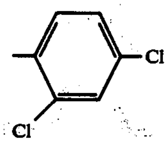 | mp 120° C |
| 120 | Cl | $CH_3$ | $CH(CH_3)CH_2CH_3$ | 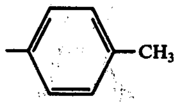 | mp 80~82° C |
| 121 | Cl | $CH_3$ | $CH(CH_3)CH_2CH_3$ | 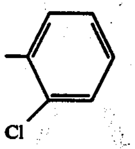 | mp 117.5~118.5° C |
| 122 | Cl | $CH_3$ | $CH(CH_3)CH_2CH_3$ | 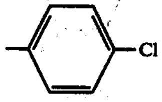 | mp 99~99.5° C |
| 123 | Cl | $CH_3$ | $CH(CH_3)CH_2CH_3$ | 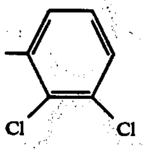 | mp 133~134° C |
| 124 | Cl | $CH_3$ | $CH_2CH(CH_3)_2$ | 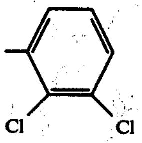 | mp 143~145° C |
| 125 | Cl | $CH_3$ | $CH_2CH(CH_3)_2$ | 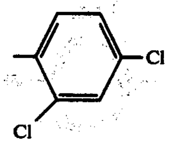 | $bp_{0.8}$ 86~87° C |
| 126 | Br | $CH_3$ | $(CH_2)_2CH_3$ | 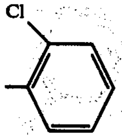 | mp 104~104.5° C |
| 127 | Br | $CH_3$ | $CH(CH_3)_2$ | 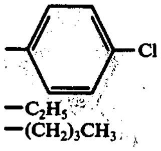 | mp 145~146.5° C |
| 128 | Cl | $CH_3$ | $-CH_2CH(OC_2H_5)_2$ | $-C_2H_5$ | $n_D^{19.5}$ 1.4874 |
| 129 | Cl | $CH_3$ | $-CH_2CH(OC_2H_5)_2$ | $-(CH_2)_3CH_3$ | $n_D^{20.5}$ 1.4852 |

-continued

| Compound | Substituent | | | | Physical |
|---|---|---|---|---|---|
| No. | X | Y | $R_1$ | $R_2$ | Property |
| 130 | Cl | $CH_3$ | $-CH_2CO_2C_2H_5$ | 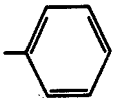 | mp 96.5~97.5° C |
| 131 | Cl | $CH_3$ | $-CH_2CO_2C_2H_5$ | 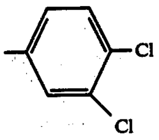 | mp 110~113° C |
| 132 | Cl | $CH_3$ | $-CH(CH_3)CO_2C_2H_5$ | 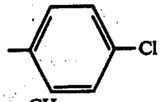 | mp 66~67° C |
| 133 | Cl | $CH_3$ | $-OCH_3$ | $-CH_3$ | $n_D^{20}$ 1.5014 |
| 134 | Cl | $CH_3$ | $-CH_2CH=CH_2$ | $-C_2H_5$ | $n_D^{22}$ 1.5166 |
| 135 | Cl | $CH_3$ | $-CH_2CH=CH_2$ | $-(CH_2)_2CH_3$ | $n_D^{20}$ 1.5102 |
| 136 | Cl | $CH_3$ | $-CH_2CH=CH_2$ | $-CH(CH_3)_2$ | $n_D^{20}$ 1.5118 |
| 137 | Cl | $CH_3$ | $-CH_2CH=CH_2$ | $-(CH_2)_3CH_3$ | $n_D^{20}$ 1.5019 |
| 138 | Cl | $CH_3$ | $-CH_2CH=CH_2$ | $-CH_2CH(CH_3)_2$ | $n_D^{19}$ 1.5061 |
| 139 | Cl | $CH_3$ | $-CH_2CH=CH_2$ | $-CH(CH_3)CH_2CH_3$ | $n_D^{20}$ 1.5103 |
| 140 | Cl | $CH_3$ | $-CH_2CH=CH_2$ | 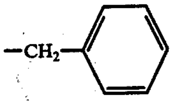 | $n_D^{21}$ 1.5520 |
| 141 | Cl | $CH_3$ | $-CH_2CH=CH_2$ | 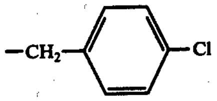 | mp 49.5~50° C |
| 142 | Cl | $CH_3$ | $-CH_2CH=CH_2$ | 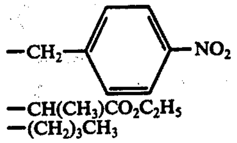 | $n_D^{22}$ 1.4936 |
| 143 | Cl | $CH_3$ | $-CH_2CH=CH_2$ | $-CH(CH_3)CO_2C_2H_5$ | $n_D^{21}$ 1.4975 |
| 144 | Cl | $CH_3$ | $-CH_2C(CH_3)=CH_2$ | $-(CH_2)_3CH_3$ | $n_D^{21}$ 1.5019 |
| 145 | Cl | $CH_3$ | $-CH_2CH=CH_2$ | 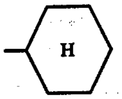 | $n_D^{25}$ 1.5212 |
| 146 | Cl | $CH_3$ | $-CH_2CH=CH_2$ | 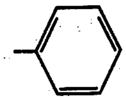 | mp 74.5~75.5° C |
| 147 | Cl | $CH_3$ | $-CH_2CH=CH_2$ | 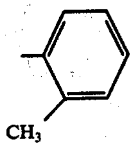 | mp 75~76.5° C |
| 148 | Cl | $CH_3$ | $-CH_2CH=CH_2$ | 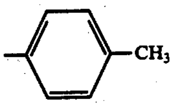 | mp 71.5~72.5° C |
| 149 | Cl | $CH_3$ | $-CH_2CH=CH_2$ | 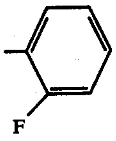 | mp 101~102° C |
| 150 | Cl | $CH_3$ | $-CH_2CH=CH_2$ | 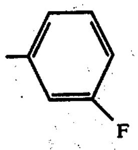 | mp 91.5~93° C |
| 151 | Cl | $CH_3$ | $-CH_2CH=CH_2$ | 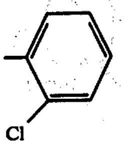 | mp 81.5~82° C |

-continued

| Compound No. | Substituent X | Y | R₁ | R₂ | Physical Property |
|---|---|---|---|---|---|
| 152 | Cl | $CH_3$ | $-CH_2CH{=}CH_2$ | 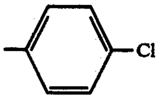 | mp 102.5~103.5° C |
| 153 | H | H | $-CH_2CH{=}CH_2$ | 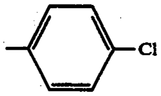 | mp 76~77° C |
| 154 | Cl | $CH_3$ | $-CH_2CH{=}CH_2$ | 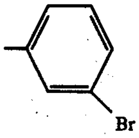 | mp 84~85° C |
| 155 | Cl | $CH_3$ | $-CH_2CH{=}CH_2$ | 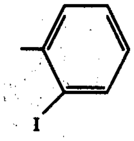 | mp 110° C |
| 156 | Cl | $CH_3$ | $-CH_2CH{=}CH_2$ | 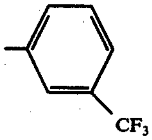 | mp 65~66° C |
| 157 | Cl | $CH_3$ | $-CH_2CH{=}CH_2$ | 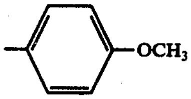 | mp 65~66° C |
| 158 | Cl | $CH_3$ | $-CH_2C(CH_3){=}CH_2$ | 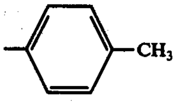 | mp 78~79° C |
| 159 | Cl | $CH_3$ | $-CH_2CH{=}CH_2$ | 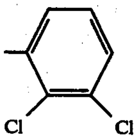 | mp 125~127° C |
| 160 | Cl | $CH_3$ | $-CH_2CH{=}CH_2$ | 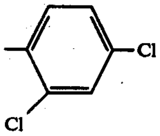 | mp 90.5~92° C |
| 161 | Cl | $CH_3$ | $-CH_2C{\equiv}CH$ | $-CH_3$ | mp 86~88° C |
| 162 | Cl | $CH_3$ | $-CH_2C{\equiv}CH$ | $-(CH_2)_2CH_3$ | $n_D^{20}$ 1.5151 |
| 163 | Cl | $CH_3$ | $-CH_2C{\equiv}CH$ | $-(CH_2)_3CH_3$ | $n_D^{20}$ 1.5118 |
| 164 | Cl | $CH_3$ | $-CH_2C{\equiv}CH$ | 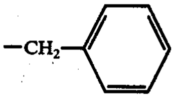 | mp 93~94.5° C |
| 165 | Cl | $CH_3$ | $-CH_2C{\equiv}CH$ | 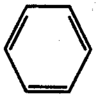 | mp 106~107° C |
| 166 | Cl | $CH_3$ | $-CH_2C{\equiv}CH$ | 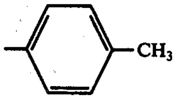 | mp 79~80.5° C |
| 167 | Cl | $CH_3$ | $-CH_2C{\equiv}CH$ | 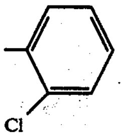 | mp 127.5° C |

-continued

| Compound No. | X | Y | Substituent $R_1$ | $R_2$ | Physical Property |
|---|---|---|---|---|---|
| 168 | Cl | $CH_3$ | $-CH_2C\equiv CH$ | 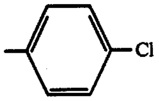 | mp 82~82.5° C |
| 169 | Cl | $CH_3$ | $-CH_2C\equiv CCH_3$ | 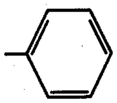 | mp 109~111° C |
| 170 | Cl | $CH_3$ | $-CH_2CH=CH_2$ | $-CH_2CH=CH_2$ | $n_D^{28}$ 1.5175 |
| 171 | Br | $CH_3$ | $-CH_2CH=CH_2$ | $-CH_2CH=CH_2$ | $n_D^{25}$ 1.5312 |
| 172 | Cl | $C_2H_5$ | $-CH_2CH=CH_2$ | $-CH_2CH=CH_2$ | $n_D^{26}$ 1.5136 |
| 173 | H | H | $-CH_2CH=CH_2$ | $-CH_2CH=CH_2$ | $n_D^{21.5}$ 1.5140 |
| 174 | $CH_3$ | $CH_3$ | $-CH_2CH=CH_2$ | $-CH_2CH=CH_2$ | $n_D^{22.5}$ 1.5070 |
| 175 | Cl | $CH_3$ | $-CH_2CH=CH_2$ | $-CH_2C(CH_3)=CH_2$ | $n_D^{20}$ 1.5184 |
| 176 | Cl | $CH_3$ | $-CH_2CH=CH_2$ | $-CH_2CH=CHCH_3$ | $n_D^{21}$ 1.5217 |
| 177 | Cl | $CH_3$ | $-CH_2CH=CH_2$ | $-CH_2C\equiv CH$ | $n_D^{21}$ 1.5279 |

The most preferable group of the isoxazolone derivatives of the above formula (I) may include the following compounds: 2-[N-isopropyl-N-(4-chlorophenyl)carbamoyl]-4-chloro-5-methyl-4-isoxazolin-3-one, 2-[N-isopropyl-N-(4-chlorophenyl)carbamoyl]-4-bromo-5-methyl-4-isoxazolin-3-one, 2-[N-isopropyl-N-(2,4-dichlorophenyl)carbamoyl]-4-chloro-5-methyl-4-isoxazolin-3-one, 2-[N-isopropyl-N-(4-methylphenyl)carbamoyl]-4-chloro-5-methyl-4-isoxazolin-3-one, 2-[N-ethyl-N-(2,4-dichlorophenyl)carbamoyl]-4-chloro-5-methyl-4-isoxazolin-3-one, 2-[N-allyl-N-isobutylcarbamoyl]-4-chloro-5-methyl-4-isoxazolin-3-one, 2-[N-isopropyl-N-(4-fluorophenyl)carbamoyl]-4-chloro-5-methyl-4-isoxazolin-3-one, 2-[N-ethyl-N-(4-chlorophenyl)carbamoyl]-4-chloro-5-methyl-4-isoxazolin-3-one, 2-[N-allyl-N-isopropylcarbamoyl]-4-chloro-5-methyl-4-isoxazolin-3-one, 2-[N-4-chlorophenyl-N-ethylcarbamoyl]-4-isoxazolin-3-one, 2-[N-isopropyl-N-(4-chlorophenyl)carbamoyl]-4-chloro-5-ethyl-4-isoxazolin-3-one, and 2-[N-ethyl-N-(2,3-cichlorophenyl)-carbamoyl]-4-chloro-5-methyl-4-isoxazolin-3-one.

The Compound No. as given in the foregoing will be hereinafter frequently referred to.

According to another aspect of this invention, there is provided a process for the preparations of the isoxazoline derivative of the formula (I). The process of this invention comprises two alternate embodiments, namely, Embodiments A and B: Embodiment A comprises reacting an isoxazolone derivative having the formula (III)

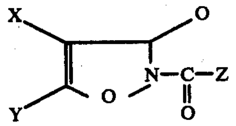

wherein X and Y are as defined above and Z represents a halogen atom with an amine having the formula (IV)

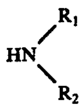

wherein $R_1$ and $R_2$ are as defined above; and Embodiment B comprises reacting a hydroxyisoxazole derivative having the formula (V)

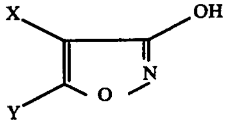

wherein X and Y are as defined above with a carbamoyl halide having the formula (VI)

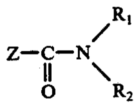

wherein $R_1$,$R_2$ and Z are as defined above.

More specifically, in one embodiment A, the starting material, i.e., the isoxazolone derivative (III) is formed by reacting the hydroxyisoxazole derivative (V) with a carbonyl halide, for example, phosgene, carbonyl dibromide and the like in an inert organic solvent, for example, hydrocarbons, e.g., benzene or toluene, halogenated hydrocarbons, e.g., methylene chloride or chloroform or ethers, e.g., diethyl ether or tetrahydrofuran. Then, the isoxazolone derivatives (III) thus formed is intimately contacted with the amine (IV) in the presence or absence of a solvent, preferably in the presence thereof. The solvent which may be employed in this reaction may be any of those solvents that could not adversely affect this reaction. Examples of such solvents include hydrocarbons, e.g., benzene, toluene or xylene; halogenated hydrocarbons, e.g., methylene chloride, chloroform, carbon tetrachloride or chlorobenzene; ethers, e.g., diethyl ether, tetrahydrofuran or dioxane; carbon disulfide; and the like. As is apparent to those skilled in the art, the reaction of this embodiment is based on dehydrohalogenation and, accordingly, the reaction may be preferably conducted in the presence of an acid binding agent.

The acid binding agent which may be employed in the reaction may be any of those agents ordinarily utilized in the art for dehydrohalogenation and, illustratively, may include inorganic bases, e.g., basic alkali metal compounds and organic bases, e.g., tertiary amines. Alternatively, the amine (IV) may be employed in a suitable amount more than that required to be a reagent, as it may act as both a reagent and an acid binding agent.

In order to make the reaction system more homogeneous, the reaction proceeding more smooth and the treatment after the reaction easier, it is more preferable to employ as an acid binding agent a tertiary amine such as straight-, saturated cyclic- and unsaturated cyclic amines, e.g., triethylamine, tributylamine, trictylamine, dimethylaniline, N-methylmorpholine, N-ethylmorpholine, N-methylpyrrolidine, N-methylpiperidine, N,N'-dimethylpiperazine, triethylenediamine, pyridine, quinoline and the like. It is unusual and most preferable to employ triethylamine because of its availability. The amount of the acid binding agent to be used is advantageously equimolar or slightly excess to that of the starting material. The reaction temperature is not critical, but the reaction may usually and smoothly proceed at room temperature to yield the desired product in a good yield, but a lower or higher temperature may be favorably applied in the reaction. The reaction period is not critical, but the reaction is usually completed within several hours. The reagent, that is, the amine (IV) may be employed in the reaction in the form of either a free base or an acid addition salt thereof. In case of the acid addition salt of the amine (IV), it is usual and preferable to use a sufficient amount of the acid binding agent not only to neutralize the acid liberated from the above acid addition salt but also to exert its action as an acid binding agent.

After completion of the reaction, the desired product (I) may be recovered from the reaction mixture by a conventional method. For instance, where the solvent is water-immiscible, insolubles are filtered off from the reaction mixture, the filtrate is washed with a suitable acid, base or water and then the solvent is distilled off to give the desired product. If necessary, the desired product thus recovered may be further purified by a conventional means, e.g., recrystallization, chromatography and the like.

In another embodiment B, the reaction can be effected by intimately contacting the starting material (V) with the carbamoyl halide (VI) in the presence or absence of an inert organic solvent, preferably in the presence thereof. The reaction in this embodiment is classified into a dehydrohalogenation reaction. However, it is not preferable to accelerate the reaction by the use of an acid binding agent, but advantageous to proceed the reaction more smoothly by heating, since the presence of the acid binding agent tends to result in the formation of an undesirable isomer of the end product, i.e., the isoxazole derivative having carbamoyloxy group at 3-position.

The solvent which may be employed in this reaction may be any of those solvents that could not adversely affect the reaction, for example, hydrocarbons, halogenated hydrocarbons, nitrohydrocarbons, ethers and the like. As shown above, the reaction may be accelerated by heating and thus it is preferred in this embodiment to employ a relatively high boiling solvent, advantageously such solvents boiling at about 80° C or higher as benzene, toluene, xylene, chlorobenzene, nitrobenzene, o,o-dichlorobenzene, trichloroethane, nitromethane, ligroin, dioxane, diethoxyethane and the like. Particularly preferable are those hydrocarbon solvents in which the hydrogen halide formed in situ during the reaction is less soluble and toluene, xylene and the like are usually employed. For the better achievement in the yield of the desired product and the acceleration of the reaction proceeding, it is also preferred to eliminate from the reaction system the hydrogen halide formed during the reaction by introducing an inert gas, e.g., gaseous nitrogen, argon or helium thereinto.

The reaction temperature is not critical, but a preferable temperature range is of about 80°–150° C and more preferable is a temperature of about 100° – 120° C.

The reaction period is not critical and varible depending upon the reaction temperature and other factors, but the reaction is usually completed within about 2 – 20 hours.

After completion of the reaction, the desired product may be recovered from the reaction mixture by a conventional method. For instance, the solvent is distilled off from the reaction mixture to give the desired product. If necessary, the end product thus recovered may be further purified by a conventional means, for example, recrystallization, chromatography and the like.

In still another aspect of this invention, there is provided a plant growth regulating composition which comprises as an active ingredient, in a sufficient amount to exert said effect, one of the isoxazolone derivatives of the above formula (I).

More particularly, there are provided the herbicidal or plant growth retarding compositions which comprise as an active ingredient an amount of about 0.5 to 95% by weight, based upon the composition, of the isoxazolone derivative of the above formula (I) and an agriculturally acceptable carrier, if necessary, together with a suitable adjuvant.

The compositions of this invention may be easily formulated into various preparation forms commonly employed in the art, for example, including finely-divided particulate solids or dusts, granules, pellets, solutions, dispersions, emulsions, wettable powders, emulsifiable concentrates and the like according to conventional techniques.

Typical solid carriers which may be employed include, for example, inorganic materials, e.g., talcs, natural and synthetic clays (kaolinites, montmorillonites, attapulgites) pumice, pyrophyllite, vermiculite, calcium carbonate, mica, powdered plaster, dolomite, diatomaceous earth, zeolite, silica, synthetic calcium and magnesium silicaes, apatite, chalk, charcoal; vegetative materials, e.g., soybean flour, tobacco dust, walnut flour, powdered wood, powdered cork, starch, crystalline cellulose; natural and synthetic polymeric materials, e.g., coumarone resin, petroleum resin, alkyd resin, polyvinyl chloride, polyalkylene glycol, ketone resin, ester gum, copal gum, dammar gum, waxes, e.g., carnauba wax, bees wax; and urea.

Typical liquid carriers which may be employed include, for example, parafinic or naphthenic hydrocarbons, e.g., kerosene, mineral oils, spindle oil, white oil; aromatic hydrocarbons, e.g., benzene, toluene, xylene, ethylbenzene, cumene, methylnaphthalene; chlorinated hydrocarbons, e.g., carbon tetrachloride, chloroform, trichloroethylene, monochlorobenzene, o-chlorotoluene; ethers, e.g., dioxane, tetrahydrofuran; ketones, e.g., acetone, methyl ethyl ketone, diisobutyl ketone, cyclohexanone, acetophenone, isophorone; esters, e.g., ethyl acetate, amyl acetate, ethyleneglycol acetate, diethyleneglycol acetate, dibutyl maleate, diethyl succinate; alcohols, e.g., methanol, n-hexanol, ethylene glycol, diethylene glycol, cyclohexanol, benzyl alcohol; ether alcohols, e.g., ethylene glycol ethyl ether, ethylene glycol phenyl ether, diethylene glycol ethyl ether, diethylene glycol butyl ether; dialkylformamides, e.g., dimethylformamide; dialkyl sulfoxides, e.g., dimethyl sulfoxide; water; and mixtures thereof.

For the purposes of emulsifying, dispersing, wetting, spreading, binding, disintegration-controlling, stabilizing, fluidity-improving, corrosion-inhibiting and others, surface active agents may be employed in the compositions of this invention. Surface active agents which can be employed may be any of non-ionic, anionic, cationic and amphoteric surface active agents commonly employed in the art, usually non-ionic and/or anionic surface active agents. Suitable non-ionic surface active agents include, for example, polyoxyethylene derivatives of higher alcohols, e.g., lauryl, stearyl or oleyl alcohol; polyoxyethylene derivatives of alkylphenols, e.g., isooctylphenol or nonylphenol; polyoxyethylene derivatives of alkylnaphthols, e.g., butylnaphthol or octylnaphthol; polyoxyethylene derivatives of higher fatty acids, e.g., palmitic, stearic or oleic acid; polyoxyethylene derivatives of dialkyl phosphoric acids, e.g., stearylphosphoric or dilauryl phosphoric acid; polyoxyethylene derivatives of amines, e.g., dodecylamine or stearyl amine; higher fatty acids esters of polyhydric alcohols, e.g., sorbitan and polyoxyethylene derivatives thereof; addition polymers of ethylene oxide and propylene oxide; and the like. Suitable anionic surface active agents include, for example, alkyl sulfate salts, e.g., sodium lauryl sulfate, oleyl sulfate amine salt; alkyl sulfonate salts, e.g., sodium dioctyl sulfosuccinate, sodium 2-ethyl hexenesulfonate; aryl sulfonate salts, e.g., sodium isopropylnaphthalene sulfonate, sodium methylene-bis-naphthalene sulfonate sodium lignin sulfonate, sodium dodecylbenzene sulfonate; and the like.

The plant growth regulating compositions of this invention may also include other adjuvants such as polymeric materials, e.g., casein, gelatin, albumin, glue, sodium alginate, carboxymethyl, cellulose, methyl cellulose, hydroxyethyl cellulose, polyvinyl alcohol and the like.

The above-mentioned carriers and adjuvants may be optionally utilized in combination therewith, depending upon the preparation forms, placed to be applied, purposes to be used and other factors.

Where the plant growth regulating composition of this invention is to be used as herbicides, the present composition may preferably include other known herbicidal substances to broaden its herbicidal spectrum and, sometimes, expect a synergistic effect. Suitable examples of such herbicidal substances include, for example, triazine derivatives, e.g., 2-methylthio-4,6-bisethylamino-1,3,5-triazine, 2-chloro-4,6-bisethylamino-1,3,5-triazine, 2-methoxy-4-ethylamino-6-isopropylamino-1,3,5-triazine; phenoxyacetic acid derivatives, e.g., 2,4-dichlorophenoxyacetic acid, 2-chloro-4-methylphenoxyacetic acid; diphenyl ether derivatives, e.g., 2,4,6-trichlorophenyl-4'-nitrophenyl ether, 2,4-dichlorophenyl-4'-nitrophenyl ether, 3,5-dimethylphenyl-4'-nitrophenyl ether; urea derivatives, e.g., 3-(3,4-dichlorophenyl)-1-methoxy-1-methylurea, 3-(3,4-dichlorophenyl)-1,1-dimethylurea; carbamate derivatives, e.g., 3-methoxycarbonylaminophenyl N-(3-methylphenyl)-carbamate, isopropyl N-(3-chlorophenyl) carbamate; uracil derivatives, e.g., 5-bromo-3-sec. butyl-6-methyluracil, 1-cyclohexyl-3,5-propylene uracil; and the like.

It is to be understood that the plant growth regulating composition of this invention may further include other known agricultural chemicals, e.g., plant growth regulators, fungicides, insecticides, acaricides, nematocides as well as fertilizers and the like.

Dusts usually contain from about 2–10 parts the active ingredient and the remainder of a solid carrier, all parts as used herein being by weight unless otherwise stated.

Wettable powders usually contain about 10–80 parts the active ingredient, the remainder being a solid carrier, a wetting and dispersing agent, if necessary, together with a protective colloid, a thixotropic agent, an anti-foaming agent and the like.

Granules usually contain about 2–10 parts the active ingredient adhering to or distributed through a solid carrier, a major portion of the remainder being a solid carrier. Average particle size of granules is usually of about 0.2–1.5 mm.

Emulsifiable concentrates usually contain about 10–50 parts the active ingredient together with about 5–20 parts a surface active agent, the remainder being a liquid carrier. If necessary, a corrosion inhibitor may be incorporated into the concentrate.

In application of the present plant growth regulating compositions in various preparation forms as depicted above, an effective amount of the active ingredient may be usually of about 30–200 g. per 10 a. for pre-emergence soil treatment of weeds in a paddy field filled with water, of about 50–400 g. per 10 a. for pre-emergence soil treatment of weeds in a field and less for soil treatment by mixing with soil. Also, for the treatment of turfs to retard their undesirable growth, an effective amount of the active ingredient may be usually of about 30–300 g. per 10 a., without any damage or yellow-turning of turfs.

In order to describe the present invention in greater details, the examples of the preparation of the isoxazolone derivatives (I) and of the formulations containing them are given below, but they are not intended to be limiting the scope of this invention. For the purpose of illustrating of the herbicidal and plant growth retarding activities of the isoxazolone derivatives (I) of this invention, some biological experiments are also shown below. All parts as used herein are by weight unless otherwise stated.

EXAMPLE 1

2-[N-ethyl-N-(2,4-dichlorophenyl)carbamoyl]-4-chloro-5-methyl-4-isoxazolin-3-one To a solution of 1.35 g. (0.01 mole) of 4-chloro-5-methyl-3-hydroxyisoxazole in 20 ml. of dry benzene was added 1 ml. of liquid phosgene and the resulting mixture was heated under reflux for 2 hours.

After completion of the reaction, the reaction mixture was allowed to cool and the excess phosgene and the benzene were distilled under reduced pressure. The residue was dissolved in 30 ml. of benzene and to the resulting solution was added dropwise 20 ml. of a benzene solution of 1.7 g. (0.009 mole) of N-ethyl-2,4-dichloroaniline and 1.0 g. of triethylamine under ice-cooling and stirring. The resulting mixture was stirred at room temperature for 4 hours. Crystalline mass separated out in situ was filtered off and thoroughly washed with ethyl ether. The combined filtrate and washings were washed successively with water, 5% aqueous sodium bicarbonate, water and then saturated aqueous sodium chloride. The ether layer was separated, dried over anhydrous sodium sulfate and the solvent was distilled off. The residue was recrystallized from isopropyl ether to give 3.05 g. of the desired product as colorless prisms melting at 101°–102° C. Yield 89.7%.

Analysis for $C_{13}H_{11}Cl_3N_2O_3$: Calculated: C: 44.66; H: 3.17; N: 8.01; Cl: 30.42; Found: C: 44.47; H: 3.19; N: 8.05; Cl: 30.48

Following the substantially same procedure as shown above, those isoxazolone compounds as recited below were prepared:

2-[N-Ethyl-N-(4-chlorophenyl)carbamoyl]-4-isoxazolin-3-one, m.p. 149° C. 51.4%.

Analysis for $C_{12}H_{11}O_3N_2Cl$: Calculated: C: 54.05; H: 4.16; N: 10.50; Cl: 13.29; Found: C: 53.85; H: 4.00; N: 10.36; Cl: 13.34

2-[N-isopropyl-N-(4-chlorophenyl)carbamoyl]-4-chloro-5-methyl-4-isoxazolin-3-one, m.p. 136°-137° C. Yield 74.3%.

Analysis for $C_{14}H_{14}Cl_2N_2O_3$: Calculated: C: 51.08; H: 4.28; N: 8.51; Cl: 21.53; Found: C: 51.28; H: 4.29; N: 8.61; Cl: 21.73 and

2-[N-isopropyl-N-(4-chlorophenyl)carbamoyl]-4-bromo-5-methyl-4-isoxazolin-3-one, m.p. 145°-146.5° C. Yield 72.1%.

Analysis for $C_{14}H_{14}BrClN_2O_3$: Calculated: C: 45.00; H: 3.78; N: 7.50; Cl: 9.49; Br: 21.39; Found: C: 45.10; H: 3.74; N: 7.57; Cl: 9.49; Br: 21.46

EXAMPLE 2

2-[N-(2-propynyl)-N-(4-methylphenyl)carbamoyl]-4-chloro-5-methyl-4-isoxazolin-3-one To a solution of 1.35 g. (0.01 mole) of 4-chloro-5-methyl-3-hydroxyisoxazole in 20 ml. of dry benzene was added 1 ml. of liquid phosgene and the resulting mixture was heated under reflux for 2 hours.

After completion of the reaction, the reaction mixture was allowed to cool and the excess phosgene and the benzene were distilled off under reduced pressure. The residue was dissolved in 30 ml. of benzene and to the resulting mixture was added dropwise 20 ml. of a benzene solution of 1.3 g. (0.009 mole) of N-(2-propynyl)-p-toluidine and 1.0 g. of triethylamine. The resulting mixture was stirred at room temperature for 4 hours. Crystalline mass separated in situ was filtered off and thoroughly washed with ethyl ether. The combined filtrate and washings were washed successively with water, 5% aqueous sodium bicarbonate, water and saturated aqueous sodium chloride. The ether layer was separated, dried over anhydrous sodium sulfate and the solvent was distilled off under reduced pressure. The residue was recrystallized from isopropyl ether to give 2.50 g. of the desired product melting at 79°.-80.5° C. Yield 83.1%.

Analysis for $C_{15}H_{13}ClN_2O_3$: Calculated: C: 59.12%; H: 4.30; N: 9.19; Cl: 11.63; Found: C: 59.03; H: 4.27; N: 9.21; Cl: 11.68

Following the substantially the same procedure as shown above, those isoxazolone compounds as recited above were prepared:

2-[N-(2-propynyl)-N-n-butylcarbamoyl]-4-chloro-5-methyl-4-isoxazolin-3-one, $n_p^{20}$ 1:5118, Yield 66.6%.

Analysis for $C_{12}H_{15}ClN_2O_3$: Calculated: C: 53.24; H: 5.59; N: 10.35; Cl: 13.09; Found: C: 53.25; H: 5.75; N: 10.17; Cl: 12.90

2-allyl-N-(2,4-dichlorophenyl)carbamoyl]-4-chloro-5-methyl-4-isoxazolin-3-one, m.p. 90.5°-92° C., Yield 55.4%.

Analysis for $C_{14}H_{11}Cl_3N_2O_3$: Calculated: C: 46.50; H: 3.07; N: 7.75; Cl: 20.41; Found: C: 46.89; H: 3.16; N: 7.91; Cl: 29.61 and 2-(N,N-diallylcarbamoyl)-4-chloro-5-methyl-4-isoxazolin-3-one, $n_D^{28}$ 1.5175, Yield 72.5%.

Analysis for $C_{11}H_{11}ClN_2O_3$: Calculated: C: 51.47; H: 5.11; N: 10.91; Cl: 13.81; Found: C: 51.30; H: 5.19; N: 10.88; Cl: 13.79

EXAMPLE 3

2-(N,N-Di-n-propylcarbamoyl)-4-chloro-5-methyl-4-isoxazolin-3-one

In a solution of 1.35 g. (0.01 mole) of 4-chloro-5-methyl-3-hydroxyisoxazole in 20 ml. of dry benzene was added 1 ml. of liquid phosgene and the resulting mixture was heated under reflux for 2 hours.

After completion of the reaction, the reaction mixture was allowed to cool and the excess phosgene and the benzene were distilled off under reduced pressure. The residue was again dissolved in 20 ml. of dry benzene and to the resulting solution was added dropwise 30 ml. of a benzene solution of 1.0 g. (0.01 mole) of di-n-propylamine and 1.0 g. of triethylamine under icecooling and stirring. The resulting mixture was stirred at room temperature for 2 hours. Crystalline mass separated in situ was filtered off and thoroughly washed with ether. The combined filtrate and washings were washed successively with water, 5%, aqueous sodium bicarbonate, water and saturated aqueous sodium chloride. The ether layer was separated and dried over anhydrous sodium sulfate. The solvent was distilled off under reduced pressure and the residue was subjected to column chromatography on silica gel (eluent, a 5:1 mixture of chloroform and ethyl acetate) to give 1.6 g. of the desired product having $n_D^{22}$ 1.4936. Yield 69.2%.

Analysis for $C_{11}H_{17}ClN_2O_3$: Calculated: C: 50.68; H: 6.57; N: 10.74; Cl: 13.60; Found: C: 51.06; H: 6.65; N: 10.57; Cl: 13.72

EXAMPLE 4

2-(N-Phenyl-N-benzylcarbamoyl)-4-chloro-5-methyl-4-isoxazolin-3-one

To a solution of 1.35 g. (0.01 mole) of 4-chloro-5-methyl-3-hydroxyisoxazole in 30 ml. of cyclohexane was added 1 ml. of liquid phosgene and the resulting mixture was heated under reflux for 2 hours.

After completion of the reaction, the reaction mixture was alloed to cool and the excess phosgene and the cyclohexane were distilled off. The residue was dissolved in 30 ml. of cyclohexane and to the resulting solution was added dropwise 30 ml. of a cyclohexane solution of 1.83 g. (0.01 mole) of benzylaniline and 1 g. of pyridine under ice-cooling and stirring. Then, the resulting mixture was stirred at room temperature for 2 hours. Crystalline mass separated in situ was separated and thoroughly washed with ether. The combined filtrate and washings were subjected to distillation under reduced pressure to remove the solvent. The residue was recrystallized from chloroform to give 2.2 g. of the desired product melting at 118°-119° C. Yield 72.3%.

Analysis for $C_{18}H_{15}ClN_2O_3$: Calculated: C: 63.07; H: 4.41; N: 8.17; Cl: 10.34; Found: C: 63.14; H: 4.45; N: 8.32; Cl: 10.51

EXAMPLE 5

2-[N-ethyl-N-(4-chlorophenyl)carbamoyl]-4-isoxazolin-3-one

A solution of 2.6 g. (0.012 mole) of N-ethyl-N-p-chlorophenylcarbamoyl chloride and 0.85 g. (0.01 mole) of 3-hydroxyisoxazole in 50 ml. of toluene was heated under reflux for 7 hours.

Thereafter, the reaction mixture was allowed to cool and the solvent was distilled off. The residue was recrystallized from isopropyl ether to give 2.0 g. of the desired product melting at 149° C. Yield 75.1%.

Analysis for $C_{12}H_{11}ClN_2O_3$: Calculated: C: 54.05; H: 4.16; N: 10.50; Cl: 13.29; Found: C: 53.85; H: 4.00; N: 10.36; Cl: 13.34

Following the substantially same procedure as shown above, those isoxazolone compounds were prepared:

2-[N-Ethyl-N-(2,4-dichlorophenyl)carbamoyl]-4-chloro-5-methyl-4-isoxazolin-3-one, m.p. 101°-102° C, Yield 56.5%.

Analysis for $C_{13}H_{11}Cl_3N_2O_3$: Calculated: C: 44.66; H: 3.17; N: 8.01; Cl: 30.42; Found: C: 44.47; H: 3.19; N: 8.05; Cl: 30.48

2-[N-isopropyl-N-(4-chlorophenyl)carbamoyl]-4-bromo-5-methyl-4-isoxazolin-3-one, m.p. 145°-146.5° C. Yield 51.8%.

Analysis for $C_{14}H_{14}Cl_2N_2O_3$: Calculated: C: 51.08; H: 4.28; N: 8.51; Cl: 21.53; Found: C: 51.04; H: 4.30; N: 8.58; Cl: 21.63

2-[N-isopropyl-N-(4-chlorophenyl)carbamoyl]-4-chloro-5-methyl-4-isoxazolin-3-one, m.p. 136°-137° C., Yield 75.0%.

Analysis for $C_{14}H_{14}Cl_2N_2O_3$: Calculated: C: 51.08; H: 4.28; N: 8.51; Cl: 21.53; Found: C: 51.28; H: 4.29; N: 8.61; Cl: 21.73

2-[N-allyl-N-(2,4-dichlorophenyl)carbamoyl]-4-chloro-5-methyl-4-isoxazolin-3-one, m.p. 90.5°-92° C., Yield 52.5%.

Analysis for $C_{14}H_{11}Cl_3N_2O_3$: Calculated: C: 46.50; H: 3.07; N: 7.75; Cl: 29.41; Found: C: 46.89; H: 3.16; N: 7.91; Cl: 29.61

2-[N-ethyl-N-(2,4-dichlorobenzyl)carbamoyl]-4-chloro-5-methyl-4-isoxazolin-3-one, m.p. 80.5°-81.5° C., Yield 57.8%.

Analysis for $C_{14}H_{13}Cl_3N_2O_3$: Calculated: C: 46.24; H: 3.60; N: 7.70; Cl: 29.24; Found: C: 46.41; H: 3.71; N: 7.66; Cl: 29.00

EXAMPLE 6

Granules

Five parts of the isoxazolone derivative of the above Compound No. 82 was finely divided and 92.5 parts of powdered silica with a particle size of 0.3 - 0.8 mm was added thereto. To the resulting mixture was sprayed an acetone solution of 2 parts of polyethylene glycol while continuously sirring in a mixer. Then, 0.5 part of white carbon was added portionwise to the mixture to make granules.

EXAMPLE 7

Granules

Three parts of the isoxazolone derivative of the above Compound No. 98 was finely divided and 15 parts of bentonite, 81.5 parts of talc and 0.5 part of sodium lignin sulfonate were added thereto. The resulting mixture was uniformly mixed in a mixer. Then, some amount of water was added and the mixture was kneaded in a kneader, extruded through screens, each having a diameter of 0.8 mm and dried in a through-flow dryer. The dried stock was made into granules by granulation and dressing of grain through a shifter.

EXAMPLE 8

Wettable powders

A mixture of 50 parts of the isoxazolone derivative of the above Compound No. 110, 43 parts of clay, 4 parts of sodium dodecylbenzenesulfonate and 3 parts of partially hydrolyzed polyvinyl alcohol was uniformly mixed in a mixer and pulverized three times in a hammer-mill to make wettable powders.

EXAMPLE 9

Emulsifiable concentrates

Twenty-five parts of the isoxazolone derivative of the above Compound No. 56, 55 parts of xylene, 10 parts of dimethylformamide, 3 parts of calcium dodecylbenzenesulfonate and 7 parts of polyoxyethylene nonylphenyl ether were uniformly mixed and dissolved to make emulsifiable concentrates.

In order to more fully illustrate the prominent plant growth regulating activity of the isoxazolone derivative of this invention, some representative experiments are shown below. In these experiments are employed wettable powders containing 50% of the isoxazolone derivative of this invention and prepared according to the procedure as shown in the above Example 8.

Experiment 1

Pre-emergence treatment of weeds in paddy fields

Appropriate amounts of the soil from a paddy field were charged into a pot and seeds of each of cockspurgrass (*Echinochloa crus-galli*) and three-square grass (*Scirpus juncoides Roxb*) as examples of narrow-leaved weeds and each of false pimpernel (*Lindernia pyxidaria L.*), Abunome (*Dopatrium junceum* Hamilton), monochoria (*Monochoria vaginalis* Presl) and toothcup (*Rotala indica* Koehne) were well admixed with the soil. Then, seedlings of rice plants and slender spikerush (*Eleocharis acicularis* Roem. et Schult) were transplanted and then the pot was filled with water. After about 4 days when the rice plant seedlings have rooted, the soil treatment was effected by the use of an emulsion of the test compound at the rate of 1000 g. of the active compound per 10 a. The herbicidal activity of the test compound was evaluated on the following scale:

| Herbicidal rating | |
|---|---|
| 0 | No control |
| 1 | Poor control |
| 2 | Fair control |
| 3 | Good control |
| 4 | Excellent control |
| 5 | Perfect control (Dead) |

The results are summarized in Table I.

Experiment 2

Post-emergence treatment of weeds in paddy fields

The substantially same procedure as shown in the above Experiment 1 was repeated except that application of the test compound was made after cockspurgrass was at 1 or 2 leaf stage.

The results are also summarized in Table I.

Experiment 3

Pre-emergence treatment of weeds in fields

Appropriate amount of the soil from a field was charged into a pot and seeds of each of cockspur-grass, manna-grass (*Digitaria adscendens* Henr.), green panicum (*Setaria viridis* Beauv.) and goose grass (*Eleusine indica* Gaertn.) as examples of narrow-leaved weeds and each of radish (*Raphanus sativus* L.), tomato (*Lycopersicon esculentum* Mill.), Inutade (*Polygonum blumei* Meisn.) and wild amaranth (*Amaranthus blitum* L.) as examples of broad-leaved plants were sowed and covered with soil. Immediately after coverage with soil, the soil surface was treated by an emulsion of the test compound at the rate of 1000 g. of the active compound per 10 a. The same herbicidal ratings as shown in the above Experiment 1 were applied.

The results are summarized in Table I.

Table I

| Compd. No. | Experiment 1 | | | | | Experiment 2 | | | | | Experiment 3 | | | | | | | |
|---|---|---|---|---|---|---|---|---|---|---|---|---|---|---|---|---|---|---|
| | Cockspur-grass | Broad-leaved weed | Three-square grass | Slender spikerush | Planted rice plant | Cockspur-grass | Broad-leaved weed | Three-square grass | Slender spikerush | Planted rice plant | Cockspur-grass | Manna-grass | Green panicum | Goose grass | Radish | Tomato | Smartweed | Wild amaranth |
| 1 | 5 | 4 | 3 | 3 | 0 | 5 | 2 | 1 | 3 | 0 | 5 | 4 | 4 | 3 | 1 | 3 | 2 | 2 |
| 2 | 5 | 4 | 3 | 3 | 0 | 4 | 3 | 3 | 2 | 0 | 5 | 4 | 3 | 2 | 0 | 2 | 2 | 3 |
| 3 | 5 | 3 | 3 | 3 | 0 | 5 | 3 | 2 | 3 | 0 | 5 | 4 | 4 | 4 | 0 | 2 | 2 | 2 |
| 4 | 5 | 5 | 4 | 4 | 0 | 5 | 5 | 3 | 4 | 0 | 5 | 5 | 5 | 4 | 2 | 2 | 4 | 5 |
| 5 | 5 | 4 | 5 | 5 | 0 | 5 | 4 | 4 | 5 | 0 | 5 | 5 | 4 | 4 | 0 | 2 | 4 | 3 |
| 6 | 5 | 5 | 4 | 4 | 1 | 5 | 4 | 4 | 3 | 0 | 5 | 5 | 5 | 4 | 2 | 3 | 5 | 5 |
| 7 | 5 | 5 | 5 | 5 | 3 | 5 | 5 | 5 | 5 | 1 | 5 | 5 | 5 | 5 | 2 | 2 | 5 | 5 |
| 8 | 5 | 4 | 4 | 4 | 0 | 5 | 3 | 3 | 4 | 0 | 5 | 5 | 5 | 5 | 2 | 4 | 5 | 4 |
| 9 | 5 | 4 | 3 | 3 | 0 | 5 | 3 | 1 | 2 | 0 | 4 | 5 | 5 | 4 | 1 | 3 | 4 | 5 |
| 10 | 5 | 4 | 4 | 5 | 3 | 5 | 4 | 3 | 4 | 0 | 4 | 5 | 4 | 4 | 0 | 2 | 4 | 3 |
| 11 | 5 | 5 | 5 | 5 | 1 | 5 | 4 | 5 | 5 | 0 | 5 | 5 | 5 | 5 | 1 | 2 | 5 | 5 |
| 12 | 5 | 5 | 4 | 5 | 0 | 5 | 5 | 3 | 4 | 0 | 5 | 5 | 5 | 5 | 0 | 4 | 5 | 5 |
| 13 | 5 | 5 | 4 | 5 | 0 | 5 | 4 | 4 | 5 | 0 | 5 | 5 | 5 | 5 | 2 | 1 | 5 | 4 |
| 14 | 5 | 5 | 4 | 4 | 0 | 5 | 4 | 2 | 3 | 0 | 3 | 5 | 4 | 5 | 0 | 0 | 3 | 2 |
| 15 | 5 | 2 | 0 | 1 | 0 | 4 | 1 | 0 | 0 | 0 | 5 | 4 | 4 | 2 | 0 | 0 | 2 | 2 |
| 16 | 4 | 2 | 4 | 3 | 0 | 4 | 2 | 2 | 1 | 0 | 4 | 3 | 4 | 3 | 0 | 1 | 2 | 2 |
| 17 | 5 | 4 | 4 | 4 | 0 | 5 | 3 | 4 | 2 | 0 | 5 | 5 | 4 | 5 | 0 | 2 | 4 | 4 |
| 18 | 5 | 5 | 5 | 5 | 1 | 5 | 5 | 5 | 5 | 0 | 5 | 5 | 5 | 5 | 2 | 4 | 5 | 5 |
| 19 | 5 | 4 | 2 | 3 | 0 | 5 | 3 | 1 | 1 | 0 | 5 | 5 | 5 | 4 | 2 | 4 | 4 | 5 |
| 20 | 5 | 5 | 3 | 4 | 0 | 5 | 4 | 3 | 3 | 0 | 5 | 5 | 4 | 5 | 0 | 2 | 5 | 5 |
| 21 | 4 | 5 | 2 | 2 | 0 | 4 | 4 | 1 | 2 | 0 | 4 | 3 | 3 | 2 | 0 | 0 | 2 | 3 |
| 22 | 5 | 4 | 3 | 3 | 0 | 5 | 3 | 3 | 2 | 0 | 5 | 5 | 4 | 5 | 0 | 3 | 4 | 3 |
| 23 | 5 | 3 | 3 | 4 | 1 | 5 | 3 | 2 | 3 | 0 | 5 | 5 | 5 | 5 | 0 | 0 | 3 | 4 |
| 24 | 5 | 2 | 3 | 3 | 0 | 5 | 2 | 2 | 3 | 0 | 5 | 5 | 4 | 4 | 0 | 1 | 3 | 2 |
| 25 | 5 | 4 | 2 | 4 | 0 | 3 | 1 | 0 | 3 | 0 | 5 | 5 | 5 | 5 | 0 | 1 | 3 | 4 |
| 26 | 4 | 4 | 2 | 3 | 0 | 4 | 3 | 3 | 3 | 0 | 4 | 5 | 3 | 4 | 2 | 1 | 3 | 1 |
| 27 | 5 | 3 | 1 | 1 | 0 | 4 | 3 | 0 | 0 | 0 | 4 | 3 | 4 | 4 | 0 | 0 | 1 | 3 |
| 28 | 5 | 5 | 5 | 5 | 1 | 5 | 4 | 5 | 5 | 0 | 5 | 5 | 5 | 5 | 1 | 0 | 5 | 5 |
| 29 | 5 | 4 | 2 | 2 | 0 | 4 | 2 | 0 | 1 | 0 | 4 | 2 | 3 | 2 | 0 | 0 | 0 | 1 |
| 30 | 5 | 2 | 4 | 4 | 0 | 5 | 1 | 4 | 3 | 0 | 4 | 3 | 3 | 4 | 0 | 0 | 1 | 2 |
| 31 | 5 | 5 | 3 | 4 | 1 | 5 | 5 | 1 | 2 | 0 | 4 | 4 | 3 | 3 | 0 | 0 | 2 | 1 |
| 32 | 5 | 4 | 2 | 2 | 0 | 4 | 2 | 0 | 0 | 0 | 2 | 2 | 0 | 1 | 0 | 0 | 0 | 0 |
| 33 | 5 | 5 | 3 | 5 | 0 | 4 | 4 | 3 | 5 | 0 | 3 | 2 | 2 | 3 | 0 | 1 | 1 | 0 |
| 35 | 5 | 5 | 5 | 4 | 0 | 5 | 5 | 5 | 0 | 0 | 5 | 5 | 5 | 5 | 1 | 1 | 4 | 3 |
| 36 | 5 | 5 | 1 | 1 | 0 | 4 | 1 | 0 | 0 | 0 | 3 | 2 | 0 | 2 | 0 | 0 | 0 | 0 |
| 37 | 5 | 5 | 5 | 4 | 0 | 5 | 4 | 4 | 4 | 0 | 5 | 5 | 5 | 5 | 0 | 1 | 3 | 2 |
| 38 | 3 | 5 | 0 | 0 | 0 | 2 | 1 | 0 | 0 | 0 | 2 | 1 | 0 | 0 | 0 | 0 | 1 | 1 |
| 39 | 5 | 5 | 3 | 3 | 0 | 5 | 4 | 2 | 1 | 0 | 5 | 5 | 5 | 5 | 0 | 0 | 2 | 2 |
| 41 | 5 | 5 | 4 | 4 | 0 | 5 | 4 | 4 | 4 | 0 | 4 | 1 | 0 | 0 | 0 | 0 | 1 | 1 |
| 42 | 5 | 3 | 0 | 1 | 0 | 3 | 0 | 0 | 0 | 0 | 2 | 3 | 0 | 0 | 0 | 0 | 0 | 0 |
| 43 | 5 | 4 | 3 | 4 | 0 | 5 | 2 | 1 | 1 | 0 | 3 | 5 | 5 | 5 | 1 | 0 | 2 | 2 |
| 45 | 5 | 5 | 4 | 3 | 0 | 4 | 3 | 3 | 4 | 0 | 4 | 2 | 0 | 0 | 0 | 0 | 1 | 0 |
| 46 | 5 | 2 | 2 | 2 | 0 | 5 | 0 | 0 | 0 | 0 | 2 | 0 | 5 | 1 | 0 | 0 | 1 | 1 |
| 47 | 5 | 3 | 0 | 2 | 0 | 5 | 1 | 0 | 0 | 0 | 4 | 1 | 0 | 0 | 0 | 0 | 0 | 0 |
| 48 | 5 | 3 | 2 | 4 | 0 | 5 | 1 | 0 | 4 | 0 | 5 | 5 | 5 | 5 | 1 | 0 | 2 | 2 |
| 49 | 5 | 3 | 1 | 1 | 0 | 5 | 3 | 0 | 1 | 0 | 4 | 1 | 0 | 1 | 0 | 0 | 2 | 1 |
| 50 | 5 | 5 | 5 | 5 | 0 | 5 | 5 | 5 | 5 | 0 | 5 | 4 | 5 | 5 | 1 | 1 | 2 | 2 |
| 51 | 5 | 5 | 5 | 5 | 0 | 5 | 5 | 5 | 5 | 0 | 5 | 5 | 5 | 4 | 0 | 1 | 3 | 3 |
| 52 | 5 | 3 | 3 | 4 | 0 | 5 | 2 | 1 | 1 | 0 | 4 | 4 | 3 | 4 | 0 | 1 | 0 | 0 |
| 53 | 5 | 5 | 5 | 5 | 0 | 5 | 5 | 5 | 5 | 0 | 5 | 5 | 5 | 5 | 1 | 2 | 5 | 3 |
| 54 | 5 | 5 | 5 | 5 | 1 | 5 | 4 | 5 | 5 | 0 | 5 | 5 | 5 | 5 | 1 | 1 | 2 | 3 |
| 55 | 5 | 5 | 5 | 5 | 1 | 5 | 4 | 5 | 5 | 0 | 5 | 5 | 5 | 5 | 1 | 1 | 3 | 3 |
| 56 | 5 | 5 | 5 | 5 | 0 | 5 | 4 | 5 | 5 | 0 | 5 | 5 | 5 | 5 | 1 | 0 | 5 | 5 |
| 57 | 5 | 5 | 4 | 5 | 0 | 5 | 4 | 5 | 5 | 0 | 5 | 5 | 5 | 5 | 1 | 1 | 4 | 4 |
| 58 | 5 | 5 | 3 | 5 | 0 | 5 | 4 | 2 | 4 | 0 | 5 | 5 | 4 | 5 | 2 | 2 | 4 | 4 |
| 59 | 5 | 5 | 5 | 5 | 0 | 5 | 5 | 5 | 5 | 0 | 5 | 5 | 5 | 5 | 2 | 2 | 5 | 5 |

Table I-continued

| Compd. No. | Experiment 1 Cockspur-grass | Experiment 1 Broad-leaved weed | Experiment 1 Three-square grass | Experiment 1 Slender spikerush | Experiment 1 Planted rice plant | Experiment 2 Cockspur-grass | Experiment 2 Broad-leaved weed | Experiment 2 Three-square grass | Experiment 2 Slender spikerush | Experiment 2 Planted rice plant | Experiment 3 Cockspur-grass | Experiment 3 Manna-grass | Experiment 3 Green panicum | Experiment 3 Goose grass | Experiment 3 Radish | Experiment 3 Tomato | Experiment 3 Smartweed | Experiment 3 Wild amaranth |
|---|---|---|---|---|---|---|---|---|---|---|---|---|---|---|---|---|---|---|
| 60 | 5 | 5 | 5 | 5 | 0 | 5 | 5 | 5 | 5 | 0 | 5 | 5 | 5 | 5 | 2 | 1 | 4 | 4 |
| 61 | 5 | 5 | 5 | 5 | 1 | 5 | 5 | 5 | 5 | 0 | 5 | 5 | 5 | 5 | 1 | 1 | 5 | 5 |
| 62 | 5 | 5 | 5 | 5 | 0 | 5 | 5 | 5 | 5 | 0 | 5 | 5 | 5 | 5 | 2 | 2 | 5 | 5 |
| 63 | 5 | 5 | 5 | 5 | 1 | 5 | 5 | 5 | 5 | 0 | 5 | 5 | 5 | 4 | 2 | 4 | 4 | 4 |
| 64 | 5 | 5 | 5 | 5 | 0 | 5 | 5 | 5 | 5 | 0 | 5 | 5 | 5 | 5 | 2 | 2 | 5 | 5 |
| 65 | 5 | 5 | 5 | 5 | 0 | 5 | 5 | 5 | 5 | 0 | 5 | 5 | 5 | 5 | 1 | 1 | 5 | 4 |
| 66 | 5 | 5 | 5 | 5 | 0 | 5 | 5 | 4 | 5 | 0 | 5 | 5 | 5 | 5 | 1 | 1 | 5 | 4 |
| 68 | 5 | 5 | 4 | 5 | 0 | 5 | 5 | 4 | 4 | 0 | 5 | 5 | 5 | 5 | 1 | 1 | 5 | 4 |
| 69 | 5 | 5 | 5 | 4 | 0 | 5 | 5 | 4 | 5 | 1 | 4 | 5 | 5 | 4 | 0 | 1 | 5 | 5 |
| 70 | 5 | 5 | 5 | 5 | 1 | 5 | 5 | 5 | 5 | 0 | 5 | 5 | 5 | 5 | 1 | 2 | 5 | 5 |
| 71 | 5 | 4 | 3 | 4 | 0 | 5 | 3 | 2 | 2 | 0 | 5 | 5 | 5 | 4 | 1 | 1 | 5 | 4 |
| 72 | 5 | 3 | 2 | 4 | 0 | 5 | 2 | 1 | 2 | 0 | 5 | 5 | 5 | 5 | 0 | 0 | 4 | 3 |
| 73 | 5 | 4 | 3 | 5 | 0 | 5 | 3 | 2 | 5 | 0 | 5 | 5 | 5 | 5 | 0 | 0 | 4 | 4 |
| 74 | 5 | 2 | 0 | 1 | 0 | 4 | 3 | 2 | 2 | 0 | 5 | 4 | 4 | 3 | 0 | 0 | 3 | 2 |
| 75 | 5 | 4 | 3 | 5 | 0 | 5 | 4 | 2 | 4 | 0 | 5 | 5 | 5 | 5 | 0 | 2 | 4 | 4 |
| 76 | 4 | 5 | 4 | 5 | 2 | 4 | 4 | 5 | 5 | 1 | 5 | 4 | 4 | 5 | 0 | 1 | 5 | 5 |
| 77 | 5 | 5 | 3 | 2 | 0 | 5 | 4 | 2 | 0 | 0 | 5 | 5 | 5 | 5 | 1 | 1 | 4 | 5 |
| 78 | 5 | 4 | 2 | 2 | 0 | 4 | 2 | 0 | 0 | 0 | 5 | 5 | 5 | 4 | 1 | 1 | 4 | 4 |
| 79 | 4 | 0 | 0 | 3 | 0 | 3 | 0 | 0 | 3 | 0 | 2 | 1 | 0 | 0 | 0 | 0 | 0 | 0 |
| 81 | 5 | 5 | 5 | 5 | 1 | 5 | 5 | 5 | 5 | 0 | 5 | 5 | 5 | 5 | 0 | 2 | 5 | 5 |
| 82 | 5 | 5 | 5 | 5 | 1 | 5 | 5 | 5 | 5 | 0 | 5 | 5 | 5 | 5 | 1 | 0 | 5 | 5 |
| 83 | 5 | 3 | 5 | 5 | 1 | 4 | 5 | 5 | 3 | 0 | 5 | 3 | 4 | 5 | 1 | 1 | 5 | 3 |
| 84 | 4 | 5 | 5 | 5 | 0 | 5 | 5 | 5 | 5 | 0 | 5 | 4 | 4 | 5 | 1 | 0 | 4 | 5 |
| 85 | 5 | 5 | 2 | 3 | 0 | 5 | 5 | 0 | 1 | 0 | 1 | 3 | 3 | 2 | 0 | 0 | 2 | 1 |
| 86 | 5 | 5 | 5 | 5 | 0 | 5 | 4 | 5 | 5 | 0 | 5 | 5 | 3 | 4 | 0 | 0 | 3 | 2 |
| 87 | 5 | 5 | 5 | 5 | 5 | 5 | 5 | 5 | 5 | 0 | 5 | 5 | 5 | 4 | 0 | 1 | 3 | 4 |
| 88 | 5 | 4 | 4 | 5 | 0 | 5 | 3 | 4 | 4 | 0 | 5 | 5 | 5 | 5 | 1 | 4 | 4 | 1 |
| 89 | 5 | 5 | 5 | 5 | 1 | 5 | 5 | 5 | 5 | 0 | 5 | 5 | 5 | 5 | 0 | 0 | 5 | 5 |
| 90 | 5 | 5 | 5 | 5 | 1 | 5 | 5 | 5 | 5 | 0 | 5 | 5 | 5 | 5 | 0 | 1 | 5 | 5 |
| 91 | 5 | 5 | 3 | 3 | 0 | 5 | 4 | 3 | 3 | 0 | 5 | 5 | 5 | 5 | 0 | 0 | 4 | 4 |
| 92 | 5 | 2 | 0 | 0 | 0 | 4 | 0 | 0 | 0 | 0 | 4 | 0 | 0 | 0 | 0 | 0 | 1 | 1 |
| 93 | 5 | 3 | 2 | 2 | 0 | 5 | 2 | 1 | 2 | 0 | 5 | 5 | 5 | 5 | 0 | 0 | 3 | 3 |
| 94 | 5 | 5 | 5 | 5 | 0 | 5 | 4 | 5 | 5 | 0 | 5 | 5 | 5 | 5 | 1 | 2 | 5 | 5 |
| 95 | 5 | 5 | 5 | 5 | 0 | 5 | 5 | 5 | 5 | 0 | 5 | 5 | 5 | 5 | 2 | 2 | 5 | 5 |
| 96 | 5 | 5 | 5 | 5 | 1 | 5 | 5 | 5 | 5 | 0 | 5 | 5 | 5 | 5 | 2 | 2 | 5 | 5 |
| 97 | 5 | 4 | 4 | 5 | 0 | 5 | 3 | 4 | 5 | 0 | 5 | 5 | 5 | 5 | 1 | 2 | 5 | 4 |
| 98 | 5 | 5 | 4 | 5 | 1 | 5 | 5 | 4 | 5 | 0 | 5 | 5 | 5 | 5 | 2 | 2 | 5 | 4 |
| 99 | 5 | 5 | 4 | 5 | 1 | 5 | 5 | 3 | 5 | 0 | 4 | 5 | 5 | 5 | 0 | 2 | 3 | 4 |
| 101 | 5 | 5 | 4 | 5 | 0 | 5 | 5 | 5 | 5 | 0 | 5 | 4 | 5 | 5 | 1 | 0 | 3 | 4 |
| 102 | 4 | 5 | 5 | 5 | 1 | 4 | 5 | 5 | 5 | 0 | 4 | 5 | 5 | 4 | 0 | 0 | 5 | 4 |
| 103 | 5 | 5 | 5 | 5 | 1 | 5 | 5 | 5 | 5 | 0 | 5 | 5 | 5 | 5 | 0 | 1 | 5 | 5 |
| 104 | 5 | 5 | 5 | 5 | 1 | 5 | 5 | 5 | 5 | 0 | 5 | 5 | 5 | 5 | 1 | 1 | 5 | 5 |
| 105 | 5 | 5 | 5 | 5 | 1 | 5 | 5 | 5 | 5 | 0 | 5 | 5 | 5 | 5 | 1 | 0 | 5 | 5 |
| 106 | 5 | 5 | 5 | 5 | 1 | 5 | 5 | 5 | 5 | 0 | 5 | 5 | 5 | 5 | 1 | 1 | 5 | 5 |
| 107 | 5 | 5 | 4 | 5 | 0 | 5 | 5 | 4 | 4 | 0 | 5 | 5 | 5 | 5 | 2 | 1 | 5 | 5 |
| 108 | 5 | 5 | 4 | 5 | 0 | 5 | 5 | 4 | 5 | 0 | 5 | 5 | 5 | 5 | 1 | 1 | 5 | 5 |
| 109 | 5 | 5 | 4 | 5 | 0 | 5 | 5 | 5 | 5 | 0 | 5 | 5 | 5 | 5 | 2 | 3 | 5 | 5 |
| 110 | 5 | 5 | 5 | 5 | 1 | 5 | 5 | 5 | 5 | 0 | 5 | 5 | 5 | 5 | 2 | 2 | 5 | 5 |
| 111 | 5 | 5 | 5 | 5 | 0 | 5 | 5 | 5 | 5 | 0 | 5 | 5 | 5 | 5 | 2 | 0 | 5 | 5 |
| 112 | 4 | 4 | 5 | 5 | 1 | 5 | 5 | 5 | 5 | 0 | 5 | 5 | 5 | 5 | 0 | 1 | 3 | 4 |
| 113 | 5 | 5 | 5 | 5 | 1 | 5 | 5 | 5 | 5 | 0 | 5 | 5 | 5 | 5 | 1 | 1 | 5 | 5 |
| 114 | 5 | 5 | 5 | 5 | 1 | 5 | 5 | 5 | 5 | 0 | 5 | 5 | 5 | 5 | 1 | 2 | 5 | 5 |
| 115 | 5 | 5 | 4 | 5 | 0 | 5 | 4 | 4 | 4 | 0 | 5 | 5 | 5 | 5 | 0 | 0 | 4 | 5 |
| 116 | 5 | 4 | 4 | 4 | 0 | 5 | 4 | 4 | 4 | 0 | 5 | 5 | 5 | 5 | 1 | 1 | 5 | 5 |
| 117 | 5 | 5 | 5 | 5 | 0 | 5 | 4 | 4 | 4 | 0 | 5 | 4 | 4 | 5 | 0 | 0 | 2 | 2 |
| 118 | 5 | 5 | 5 | 5 | 0 | 5 | 5 | 5 | 5 | 0 | 5 | 5 | 5 | 5 | 1 | 1 | 5 | 4 |

Table I-continued

| | Experiment 1 | | | | | Experiment 2 | | | | | Experiment 3 | | | | | | | |
|---|---|---|---|---|---|---|---|---|---|---|---|---|---|---|---|---|---|---|
| Compd. No. | Cockspur-grass | Broad-leaved weed | Three-square grass | Slender spikerush | Planted rice plant | Cockspur-grass | Broad-leaved weed | Three-square grass | Slender spikerush | Planted rice plant | Cockspur-grass | Manna-grass | Green panicum | Goose grass | Radish | Tomato | Smartweed | Wild amaranth |
| 119 | 5 | 5 | 5 | 5 | 0 | 5 | 5 | 5 | 5 | 0 | 5 | 5 | 5 | 5 | 1 | 2 | 5 | 5 |
| 120 | 5 | 5 | 4 | 5 | 0 | 5 | 5 | 3 | 5 | 0 | 5 | 5 | 5 | 5 | 1 | 1 | 4 | 5 |
| 121 | 5 | 5 | 5 | 5 | 1 | 5 | 5 | 5 | 5 | 0 | 5 | 5 | 5 | 5 | 1 | 0 | 5 | 5 |
| 122 | 5 | 5 | 5 | 5 | 0 | 5 | 5 | 5 | 5 | 0 | 5 | 5 | 5 | 5 | 1 | 2 | 4 | 5 |
| 123 | 5 | 5 | 5 | 5 | 0 | 5 | 5 | 5 | 5 | 0 | 5 | 5 | 5 | 5 | 1 | 1 | 5 | 5 |
| 124 | 5 | 5 | 5 | 5 | 1 | 5 | 5 | 5 | 5 | 0 | 5 | 5 | 5 | 5 | 3 | 2 | 5 | 5 |
| 125 | 5 | 5 | 5 | 5 | 0 | 5 | 5 | 5 | 5 | 0 | 5 | 5 | 5 | 5 | 2 | 2 | 5 | 4 |
| 126 | 5 | 5 | 4 | 5 | 1 | 5 | 5 | 4 | 4 | 0 | 5 | 5 | 5 | 5 | 0 | 1 | 5 | 4 |
| 127 | 5 | 5 | 5 | 5 | 0 | 5 | 5 | 5 | 5 | 0 | 5 | 5 | 5 | 5 | 2 | 1 | 5 | 5 |
| 128 | 5 | 1 | 2 | 2 | 0 | 2 | 0 | 0 | 0 | 0 | 3 | 3 | 2 | 2 | 0 | 0 | 2 | 0 |
| 129 | 5 | 1 | 2 | 2 | 0 | 1 | 0 | 0 | 0 | 0 | 3 | 3 | 2 | 3 | 0 | 2 | 2 | 1 |
| 130 | 5 | 4 | 4 | 4 | 0 | 5 | 3 | 4 | 4 | 0 | 5 | 5 | 5 | 5 | 0 | 1 | 4 | 5 |
| 131 | 5 | 4 | 4 | 5 | 0 | 5 | 4 | 4 | 4 | 0 | 5 | 4 | 4 | 5 | 1 | 1 | 4 | 4 |
| 132 | 5 | 5 | 5 | 5 | 0 | 5 | 5 | 5 | 5 | 0 | 5 | 5 | 5 | 5 | 2 | 2 | 5 | 5 |
| 133 | 5 | 5 | 3 | 2 | 0 | 5 | 4 | 2 | 0 | 0 | 4 | 4 | 5 | 2 | 0 | 0 | 2 | 2 |
| 134 | 5 | 3 | 4 | 4 | 0 | 5 | 2 | 4 | 3 | 0 | 5 | 5 | 5 | 5 | 1 | 2 | 5 | 5 |
| 135 | 5 | 2 | 5 | 5 | 0 | 5 | 2 | 5 | 5 | 0 | 5 | 5 | 5 | 5 | 2 | 4 | 4 | 5 |
| 136 | 5 | 3 | 5 | 5 | 1 | 5 | 2 | 5 | 5 | 0 | 5 | 5 | 5 | 5 | 2 | 4 | 5 | 5 |
| 137 | 5 | 5 | 5 | 5 | 1 | 5 | 5 | 5 | 5 | 0 | 5 | 5 | 5 | 5 | 2 | 3 | 5 | 5 |
| 138 | 5 | 5 | 5 | 5 | 1 | 5 | 5 | 5 | 5 | 0 | 5 | 5 | 5 | 5 | 2 | 4 | 5 | 5 |
| 139 | 5 | 5 | 5 | 5 | 0 | 5 | 5 | 5 | 5 | 0 | 5 | 5 | 5 | 5 | 0 | 4 | 4 | 5 |
| 140 | 5 | 5 | 4 | 5 | 0 | 5 | 5 | 5 | 5 | 0 | 5 | 5 | 5 | 5 | 1 | 4 | 4 | 4 |
| 141 | 5 | 5 | 4 | 5 | 0 | 5 | 5 | 4 | 5 | 0 | 5 | 5 | 5 | 5 | 1 | 2 | 2 | 3 |
| 142 | 5 | 5 | 5 | 5 | 0 | 5 | 4 | 5 | 5 | 0 | 5 | 5 | 5 | 5 | 1 | 4 | 5 | 5 |
| 143 | 5 | 5 | 5 | 5 | 1 | 5 | 5 | 5 | 5 | 0 | 5 | 5 | 5 | 5 | 1 | 1 | 5 | 5 |
| 144 | 5 | 5 | 5 | 5 | 0 | 5 | 4 | 4 | 5 | 0 | 5 | 5 | 5 | 5 | 1 | 1 | 3 | 4 |
| 145 | 5 | 5 | 5 | 5 | 1 | 5 | 5 | 5 | 5 | 0 | 5 | 5 | 5 | 5 | 0 | 1 | 3 | 4 |
| 146 | 5 | 5 | 5 | 5 | 0 | 5 | 5 | 5 | 5 | 0 | 5 | 5 | 5 | 5 | 1 | 2 | 5 | 5 |
| 147 | 5 | 5 | 4 | 5 | 0 | 5 | 5 | 4 | 5 | 0 | 5 | 5 | 5 | 5 | 1 | 2 | 5 | 5 |
| 148 | 5 | 5 | 5 | 5 | 0 | 5 | 4 | 5 | 5 | 0 | 5 | 5 | 5 | 5 | 0 | 2 | 4 | 5 |
| 149 | 5 | 5 | 5 | 5 | 1 | 5 | 5 | 5 | 5 | 0 | 5 | 5 | 5 | 5 | 0 | 4 | 4 | 5 |
| 150 | 5 | 5 | 5 | 5 | 0 | 5 | 4 | 5 | 5 | 0 | 5 | 5 | 4 | 5 | 2 | 2 | 5 | 5 |
| 151 | 5 | 5 | 5 | 5 | 1 | 5 | 5 | 5 | 5 | 0 | 5 | 5 | 5 | 5 | 2 | 2 | 5 | 3 |
| 152 | 5 | 5 | 5 | 5 | 1 | 5 | 5 | 5 | 5 | 0 | 5 | 5 | 5 | 5 | 2 | 3 | 3 | 4 |
| 153 | 5 | 5 | 4 | 5 | 0 | 5 | 4 | 4 | 4 | 0 | 5 | 5 | 5 | 5 | 0 | 0 | 5 | 5 |
| 154 | 5 | 5 | 5 | 5 | 1 | 5 | 5 | 4 | 5 | 0 | 2 | 4 | 4 | 5 | 2 | 2 | 4 | 5 |
| 155 | 5 | 5 | 4 | 5 | 0 | 5 | 5 | 4 | 5 | 0 | 5 | 5 | 5 | 5 | 1 | 2 | 5 | 5 |
| 156 | 5 | 4 | 5 | 5 | 1 | 5 | 5 | 5 | 5 | 0 | 3 | 3 | 2 | 5 | 1 | 1 | 5 | 5 |
| 157 | 5 | 4 | 3 | 5 | 0 | 5 | 3 | 3 | 4 | 0 | 5 | 5 | 5 | 5 | 1 | 1 | 3 | 5 |
| 158 | 5 | 3 | 4 | 4 | 0 | 4 | 2 | 3 | 4 | 0 | 5 | 5 | 5 | 5 | 0 | 2 | 3 | 1 |
| 159 | 5 | 5 | 5 | 5 | 1 | 5 | 5 | 5 | 5 | 0 | 5 | 5 | 5 | 5 | 2 | 2 | 5 | 5 |
| 160 | 5 | 5 | 5 | 5 | 1 | 5 | 5 | 5 | 5 | 0 | 5 | 5 | 5 | 5 | 1 | 1 | 5 | 5 |
| 161 | 5 | 5 | 5 | 5 | 1 | 5 | 5 | 5 | 5 | 0 | 5 | 5 | 5 | 5 | 2 | 4 | 4 | 5 |
| 162 | 5 | 5 | 5 | 5 | 2 | 5 | 5 | 5 | 5 | 0 | 5 | 5 | 5 | 5 | 4 | 4 | 5 | 5 |
| 163 | 5 | 5 | 5 | 5 | 2 | 5 | 5 | 5 | 5 | 0 | 5 | 5 | 5 | 5 | 2 | 4 | 5 | 5 |
| 164 | 5 | 5 | 5 | 5 | 0 | 5 | 5 | 5 | 5 | 0 | 5 | 5 | 5 | 5 | 0 | 2 | 3 | 5 |
| 165 | 5 | 5 | 5 | 5 | 1 | 5 | 5 | 5 | 5 | 0 | 5 | 5 | 5 | 5 | 4 | 4 | 5 | 5 |
| 166 | 5 | 5 | 5 | 5 | 0 | 5 | 5 | 4 | 5 | 0 | 5 | 5 | 5 | 5 | 1 | 2 | 4 | 5 |
| 167 | 5 | 5 | 4 | 5 | 0 | 5 | 4 | 3 | 5 | 0 | 5 | 5 | 5 | 4 | 1 | 0 | 4 | 4 |
| 168 | 5 | 5 | 4 | 4 | 0 | 5 | 5 | 4 | 3 | 0 | 5 | 5 | 5 | 5 | 1 | 0 | 4 | 5 |
| 169 | 5 | 5 | 4 | 4 | 0 | 5 | 5 | 4 | 5 | 0 | 4 | 3 | 5 | 5 | 2 | 4 | 2 | 4 |
| 170 | 5 | 5 | 5 | 5 | 1 | 5 | 5 | 5 | 5 | 0 | 5 | 5 | 5 | 5 | 2 | 2 | 5 | 5 |
| 171 | 5 | 5 | 5 | 5 | 1 | 5 | 5 | 5 | 5 | 0 | 5 | 5 | 5 | 5 | 2 | 2 | 5 | 5 |
| 172 | 5 | 4 | 5 | 5 | 0 | 5 | 5 | 5 | 5 | 0 | 5 | 3 | 4 | 4 | 1 | 1 | 4 | 5 |
| 173 | 5 | 3 | 4 | 5 | 0 | 5 | 3 | 4 | 4 | 0 | 5 | 5 | 5 | 5 | 2 | 4 | 5 | 5 |
| 174 | 5 | 1 | 0 | 0 | 0 | 4 | 1 | 0 | 0 | 0 | 5 | 5 | 5 | 5 | 1 | 1 | 3 | 3 |
| 175 | 5 | 5 | 5 | 5 | 1 | 5 | 5 | 5 | 5 | 0 | 5 | 5 | 5 | 5 | 2 | 4 | 4 | 5 |
| 176 | 5 | 5 | 5 | 5 | 1 | 5 | 5 | 5 | 5 | 0 | 5 | 5 | 5 | 5 | 2 | 4 | 4 | 5 |
| 177 | 5 | 5 | 5 | 5 | 1 | 5 | 5 | 5 | 5 | 0 | 5 | 5 | 5 | 5 | 2 | 2 | 5 | 5 |

Experiment 4

Herbicidal test against weeds in field

Seeds of manna-grass were sowed on the soil from a field, which was charged into a pot, and covered with the soil. Immediately, the soil surface was treated with an emulsion of the test compound at the indicated concentration and the dose of each test compound was investigated to exert a herbicidal activity of 80% or higher.

The herbicidal ratings are as follows:

1. 80% or higher herbicidal activity obtained with 200 g. of the test compound per 10 a.
2. 80% or higher herbicidal activity obtained with 100 g. of the test compound per 10 a.
3. 80% or higher herbicidal activity obtained with 50 g. of the test compound per 10 a.
4. 80% or higher herbicidal activity obtained with 25 g. of the test compound per 10 a.
5. 80% or higher herbicidal activity obtained with 12.5 g. of the test compound per 10 a.

The results are summarized in Table II

Table II

| Compound No. | Herbicidal Activity | Compound No. | Herbicidal Activity |
|---|---|---|---|
| 55 | 2 | 134 | 2 |
| 56 | 2 | 135 | 3 |
| 62 | 3 | 136 | 3 |
| 64 | 3 | 137 | 3 |
| 72 | 1 | 138 | 3 |
| 75 | 1 | 139 | 1 |
| 77 | 1 | 149 | 2 |
| 81 | 3 | 151 | 2 |
| 82 | 4 | 152 | 1 |
| 90 | 3 | 160 | 2 |
| 94 | 1 | 164 | 4 |
| 98 | 3 | 166 | 4 |
| 103 | 2 | 170 | 4 |
| 105 | 3 | 175 | 3 |
| 106 | 4 | 177 | 3 |
| 110 | 5 | | |
| 120 | 1 | | |
| 127 | 4 | | |

It will be apparent from the above results that the isoxazolone derivatives (I) of this invention exert high herbicidal activity against manna-grass known as one of the resistant weeds in fields, orchards and the like in an extremely small dose; in particular, the isoxazolone derivatives of the above Compound Nos. 82, 127, 106 and 110 and 164, 166 and 170 show a potent herbicidal activity against manna-grass in doses of 12.5 g. or less and 25 g. or less per 10 a., respectively, which should be considered unexpected in view of the prior art herbicides.

Experiment 5

Growth retarding activity test on turfs

Appropriate amount of soil was charged into a pot with a diameter of 9 cm. and seeds of bentgrass (Penncross) were sowed over the whole soil surface. Then, the soil surface was covered with soil with a thickness of 5 mm. After the grass grew to a height of about 30 mm. in about 2 weeks, the grass was cut at the height of 10 mm and 7 ml. of an emulsion of the test compound at the indicated concentration (containing as a spreader 0.01% of Shingramin, tradename, a mixture of polyoxyethylene dodecyl ether, polyoxyethylene alkylaryl ether and ligninsulfonates available from Sankyo Company Limited, Japan) was applied by spraying to the plants in each pot. Heights of the grass were measured at intervals of 10 days after the application of the test compound and growth retarding degree was determined in comparison with controls.

The growth retarding activity ratings are as follows:

0. No control, with 100 g. of the test compound per a.
1. 0–25% control with 100 g. of the test compound per a.
2. 25–50% control with 100 g. of the test compound per a.
3. More than 50% control with 100 g. of the test compound per a.
4. More than 50% control with 75 g. of the test compound per a.
5. More than 50% control with 50 g. of the test compound per a.
6. More than 50% control with 25 g. of the test compound per a.
7. More than 50% control with 12.5 g. of the test compound per a.
8. More than 50% control with 6.25 g of the test compound per a.

The results are summarized in Table III.

Table III

| Compound No. | Growth retarding degree | Compound No. | Growth retarding degree |
|---|---|---|---|
| 32 | 5 | 54 | 5 |
| 33 | 3 | 55 | 6 |
| 34 | 3 | 56 | 7 |
| 35 | 5 | 57 | 6 |
| 36 | 5 | 58 | 4 |
| 37 | 5 | 59 | 7 |
| 38 | 3 | 60 | 6 |
| 39 | 5 | 61 | 6 |
| 40 | 3 | 62 | 7 |
| 41 | 3 | 63 | 8 |
| 42 | 3 | 64 | 8 |
| 43 | 3 | 65 | 7 |
| 44 | 3 | 66 | 8 |
| 45 | 3 | 67 | 6 |
| 46 | 3 | 68 | 5 |
| 47 | 3 | 69 | 8 |
| 48 | 5 | 70 | 5 |
| 49 | 3 | 71 | 4 |
| 50 | 7 | 72 | 3 |
| 51 | 3 | 73 | 5 |
| 52 | 3 | 74 | 5 |
| 53 | 3 | 75 | 5 |
| 76 | 6 | 102 | 6 |
| 77 | 5 | 103 | 5 |
| 78 | 4 | 104 | 5 |
| 79 | 3 | 105 | 8 |
| 80 | 3 | 106 | 8 |
| 81 | 5 | 107 | 7 |
| 82 | 8 | 108 | 7 |
| 83 | 6 | 109 | 6 |
| 84 | 8 | 110 | 8 |
| 85 | 5 | 111 | 8 |
| 86 | 5 | 112 | 6 |
| 87 | 5 | 113 | 5 |
| 88 | 5 | 114 | 7 |
| 89 | 5 | 115 | 3 |
| 90 | 6 | 116 | 8 |
| 91 | 4 | 117 | 5 |
| 92 | 6 | 118 | 6 |
| 93 | 3 | 119 | 5 |
| 94 | 5 | 120 | 6 |
| 95 | 7 | 121 | 7 |
| 96 | 6 | 122 | 5 |
| 97 | 8 | 123 | 5 |
| 98 | 6 | 124 | 5 |
| 99 | 7 | 125 | 4 |
| 100 | 5 | 126 | 7 |
| 101 | 7 | 127 | 8 |
| 128 | 3 | 153 | 7 |
| 129 | 5 | 154 | 4 |
| 130 | 4 | 155 | 3 |
| 131 | 3 | 156 | 4 |
| 132 | 4 | 157 | 7 |
| 133 | 4 | 158 | 4 |
| 134 | 6 | 159 | 6 |
| 135 | 8 | 160 | 7 |
| 136 | 8 | 161 | 7 |
| 137 | 8 | 162 | 8 |
| 138 | 8 | 163 | 7 |
| 139 | 7 | 164 | 5 |
| 140 | 7 | 165 | 6 |

Table III-continued

| Compound No. | Growth retarding degree | Compound No. | Growth retarding degree |
|---|---|---|---|
| 141 | 7 | 166 | 6 |
| 142 | 7 | 167 | 7 |
| 143 | 6 | 168 | 8 |
| 144 | 5 | 169 | 5 |
| 145 | 7 | 170 | 7 |
| 146 | 8 | 171 | 8 |
| 147 | 5 | 172 | 7 |
| 148 | 6 | 173 | 6 |
| 149 | 7 | 174 | 8 |
| 150 | 3 | 175 | 8 |
| 151 | 7 | 176 | 8 |
| 152 | 6 | 177 | 8 |

It will be apparent from the above results that the isoxazolone derivatives (I) of this invention, in particular, the isoxazolone derivatives of the above Compound Nos. 63, 64, 66, 69, 82, 84, 97, 105, 106, 110, 111, 116, 127, 135, 136, 137, 138, 146, 162, 168, 171 174, 175, 176 and 177, show prominent growth retarding activity against turfs by post-emergence treatment.

What is claimed is:

1. A compound having the formula

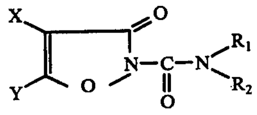

wherein X is hydrogen atom, lower alkyl or halogen atom; Y is hydrogen atom, lower alkyl or phenyl; and $R_1$ and $R_2$ may be the same or different and each represents lower alkyl, dialkoxyalkyl having from 1 to 3 carbon atoms in each of the alkyl and alkoxy portions, alkoxycarbonylalkyl having 1 to 4 carbon atoms in the alkoxy portion and 1 to 2 carbons in the alkyl portion, cycloalkyl having from 5 to 7 carbon atoms, alkenyl having from 3 to 5 carbon atoms, alkynyl having from 3 to 4 carbon atoms, lower alkoxy, substituted phenyl having the formula

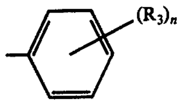

wherein $R_3$ is lower alkyl, halogen, lower alkoxy, alkoxycarbonyl having 1 to 4 carbon atoms in the alkoxy portion, nitro or trifluoromethyl, and n is an integer from 0 to 3 and $R_3$ may be the same or different, or substituted aralkyl having the formula

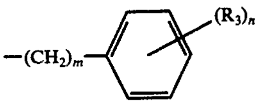

wherein *m* is 1 or 2 and $R_3$ and n are as defined above.

2. The compound according to claim 1 wherein X is hydrogen atom, chlorine atom or bromine atom, Y is hydrogen atom, methyl or ethyl, $R_1$ is allyl or alkyl of 2 or 3 carbon atoms and $R_2$ is alkyl of 3 or 4 carbon atoms or phenyl which is substituted with one or two members selected from alkyl of 1 to 4 carbon atoms, halogen, alkoxy of 1 to 4 carbon atoms, nitro, alkoxycarbonyl of 1 to 4 carbon atoms in the alkoxy moiety and trifluoromethyl group.

3. 2-[N-Isopropyl-N-(4-chlorophenyl)carbamoyl]-4-chloro-5-methyl-4-isoxazolin-3-one.

4. 2-[N-Isopropyl-N-(4-chlorophenyl)carbamoyl]-4-bromo-5-methyl-4-isoxazolin-3-one.

5. 2-[N-Isopropyl-N-(2,4-dichlorophenyl)carbamoyl]-4-chloro-5-methyl-4-isoxazolin-3-one.

6. 2-[N-Ethyl-N-(2,4-dichlorophenyl)carbamoyl]-4-chloro-5-methyl-4-isoxazolin-3-one.

7. 2-[N-Isopropyl-N-(4-methylphenyl)carbamoyl]-4-chloro-5-methyl-4-isoxazolin-3-one.

8. 2-[N-Allyl-N-isobutylcarbamoyl]-4-chloro-5-methyl-4-isoxazolin-3-one.

9. 2-[N-Isopropyl-N-(4-fluorophenyl)carbamoyl]-4-chloro-5-methyl-4-isoxazolin-3-one.

10. 2-[N-Ethyl-N-(4-chlorophenyl)carbamoyl]-4-chloro-5-methyl-4-isoxazolin-3-one.

11. 2-[N-allyl-N-isopropylcarbamoyl]-4-chloro-5-methyl-4-isoxazolin-3-one.

12. 2-[N-(4-Chlorophenyl)-N-ethylcarbamoyl]-4-isoxazolin-3-one.

13. 2-[N-Isopropyl-N-(4-chlorophenyl)carbamoyl]-4-chloro-5-ethyl-4-isoxazolin-3-one.

14. 2-[N-Ethyl-N-(2,3-dichlorophenyl)carbamoyl]-4-chloro-5-methyl-4-isoxazolin-3-one.

* * * * *